United States Patent
Mutel et al.

(10) Patent No.: US 6,927,232 B2
(45) Date of Patent: Aug. 9, 2005

(54) PHENYLETHYNYL AND STYRYL DERIVATIVES OF IMIDAZOLE AND FUSED RING HETEROCYCLES

(75) Inventors: Vincent Mutel, Mulhouse (FR); Jens-Uwe Peters, Grenzach-Wyhlen (DE); Juergen Wichmann, Steinen (DE)

(73) Assignee: Hoffman-La Roche Inc., Nutley, NJ (US)

(*) Notice: Subject to any disclaimer, the term of this patent is extended or adjusted under 35 U.S.C. 154(b) by 0 days.

(21) Appl. No.: 10/407,929

(22) Filed: Apr. 4, 2003

(65) Prior Publication Data

US 2003/0225070 A1 Dec. 4, 2003

Related U.S. Application Data

(62) Division of application No. 09/996,641, filed on Nov. 28, 2001, now Pat. No. 6,706,707.

(30) Foreign Application Priority Data

Dec. 4, 2000 (EP) ............................................. 00126615

(51) Int. Cl.[7] ................. A61K 31/4164; A61K 31/415; C07D 233/54
(52) U.S. Cl. ................. 514/399; 548/335.1; 548/341.1; 548/356.1; 548/373.1; 548/376.1; 514/403
(58) Field of Search .......................... 548/341.1, 335.1, 548/356.1, 373.1, 376.1; 514/399, 403

(56) References Cited

U.S. PATENT DOCUMENTS

| | | |
|---|---|---|
| 3,303,199 A | 2/1967 | Doebel et al. |
| 3,341,548 A | 9/1967 | Hoffer |
| 4,352,818 A | 10/1982 | Hunkeler et al. |
| 4,711,962 A | 12/1987 | Leone-Bay |

FOREIGN PATENT DOCUMENTS

| | | |
|---|---|---|
| DE | 2035905 | 2/1972 |
| EP | 059 390 | 9/1982 |
| WO | WO 91/00277 | 1/1991 |
| WO | WO 99/02497 | 1/1999 |
| WO | WO 99/08678 | 2/1999 |
| WO | WO 01/16121 | 3/2001 |

OTHER PUBLICATIONS

Sakamoto et al., *Chem. Pharm. Bull.*, vol. 35(2), pp. 823–828 (1987.
Robert D. Miller, *Chem. Mater.*, vol. 6(7), pp. 1023–1032 (1994).
Rapoport et al., *Environ. Health Perspect.*, vol. 67, pp. 41–45 (1986).

(Continued)

*Primary Examiner*—Golam M M Shameem
(74) *Attorney, Agent, or Firm*—George W. Johnston; Patricia S. Rocha-Tramaloni; Kimberly J. Prior

(57) ABSTRACT

This invention relates to the treatment of mGluR5 receptor mediated disorders, which comprises administering to a person in need of treatment a compound having the formula

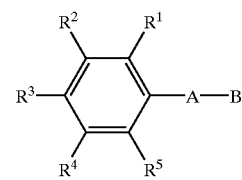

I wherein $R^1$, $R^2$, $R^3$, $R^4$ and $R^5$ are as defined in the description, A signifies —CH=CH— or —C≡C—; and B signifies

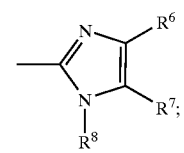

B1)

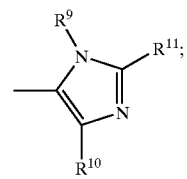

B2)

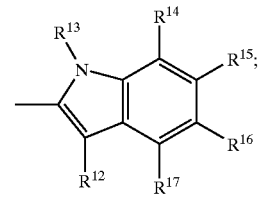

B3)

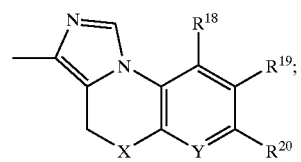

B4)

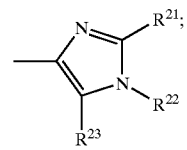

B5)

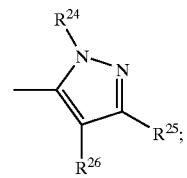

B6)

wherein $R^6$ to $R^{26}$, X and Y are as defined herein.

15 Claims, No Drawings

OTHER PUBLICATIONS

Bond et al., *Synth, Commun.*, vol. 19, pp. 2551–2566 (1989).
Sintas et al., *Journal of Labelled Compds. & Radiopharmaceuticals*, vol. 39, pp. 677–684 (1997).
Hoffer et al., *J.Med. Chem.*, vol. 17(9), pp. 1019–1020 (1974).
Ohpa etal., *Chem. Pharm. Bull.*, vol. 42, pp. 1784–1790 (1994).
Kulkarni et al., *Aust. J. Chem.*, vol. 40(8), pp. 1399–1413 (1987).
Vasileuskii et al., *Bull. Acad. Sci USSR Div. Chem. Sci.*, pp. 626–628 (1983).
F.J. LaRonde et al., *Inorg. Chim. Acta*, vol. 296 (1), pp. 208–221 (1999).

Shafiee et al., *J. Heterocyclic Chem.*, vol. 33, pp. 671–673 (1996).

Shafiee et al., *J. Heterocyclic Chem.*, vol. 35, pp. 607–610 (1998).

Ivanova et al., *Chem Heterocycl. Comp.*, vol. 36(2), pp. 262–264 (2000).

G. H. Wadsworth, *J.Chem. Soc.*, vol. 57, pp. 11 (1890).

Cornforth and Cookson, *J. Chem. Soc.*, pp. 1085–1087 (1952).

W. Ross et al., *J. Med. Chem.*, vol. 15(10), pp. 1035–1040 (1972).

PHENYLETHYNYL AND STYRYL DERIVATIVES OF IMIDAZOLE AND FUSED RING HETEROCYCLES

CROSS-REFERENCE TO RELATED APPLICATION

This application is a divisional of Ser. No. 09/996,641, filed Nov. 28, 2001 now U.S. Pat. No. 6,706,707.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and pain. Selective mGluR5 antagonists are especially useful for the treatment of anxiety and pain.

SUMMARY OF THE INVENTION

The present invention is a method of treatment of mGluR5 receptor mediated disorders by administering a therapeutically effective amount phenylethenyl and phenylethynyl derivatives of the compound formula

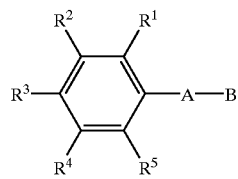

I wherein $R^1, R^2, R^3, R^4$ and $R^5$, are independently selected from the group consisting of hydrogen, lower alkyl, —$(CH_2)_n$-halogen, lower alkoxy, —$(CH_2)_n$—NRR', —$(CH_2)_n$—N(R)—C(O)-lower alkyl, aryl or heteroaryl which is unsubstituted or substituted by one or more lower alkyl residues;

R, R' and R" are independently selected from the group consisting of hydrogen and lower alkyl;

A is selected from the group consisting of —CH=CH— or —C≡C—; and

B is selected from the group consisting of

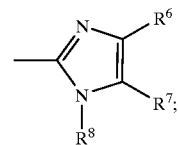

B1)

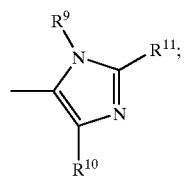

B2)

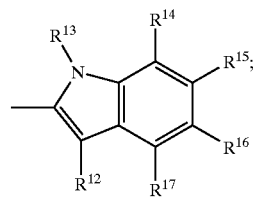

B3)

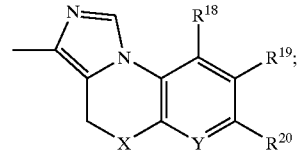

B4)

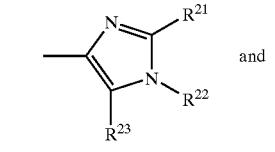

B5) and

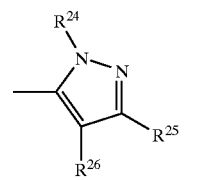

B6)

wherein
- R⁶ is selected from the group consisting of hydrogen, lower alkyl, —(CH₂)ₙ—C(O)OR and halogen;
- R⁷ is selected from the group consisting of hydrogen, lower alkyl, —(CH₂)ₙ—C(O)OR', halogen, nitro, unsubstituted heteroaryl and heteroaryl substituted by lower alkyl or cycloalkyl;
- R⁸ is selected from the group consisting of hydrogen, lower alkyl, —(CH₂)ₙ—OH, —(CH₂)ₙ—C(O)OR" and aryl;
- R⁹ is lower alkyl;
- R¹⁰ is selected from the group consisting of hydrogen, lower alkyl and halogen;
- R¹¹ is selected from the group consisting of hydrogen and alkyl;
- R¹² is —(CH₂)ₙ—N(R)—C(O)-lower alkyl;
- R¹³ selected from the group consisting of hydrogen and lower alkyl;
- R¹⁴, R¹⁵, R¹⁶ and R¹⁷ are independently selected from the group consisting of, hydrogen, lower alkyl, —(CH₂)ₙ-halogen and lower alkoxy;
- R¹⁸, R¹⁹ and R²⁰ are independently selected from the group consisting of hydrogen, lower alkyl, —(CH₂)ₙ-halogen and lower alkoxy;
- R²¹ is hydrogen or lower alkyl;
- R²² is selected from the group consisting of hydrogen, lower alkyl and lower alkyl with at least one substituent selected from the group consisting of hydroxy or halogen;
- R²³ is selected from the group consisting of hydrogen, lower alkyl lower alkanoyl and nitro;
- R²⁴, R²⁵ and R²⁶, are independently selected from the group consisting of hydrogen and lower alkyl;
- n is 0, 1, 2, 3, 4, 5 or 6;
- X is —CH₂—, —O— or —S—; and
- Y is —CH= or —N=;

or a pharmaceutically acceptable salt thereof.

Some compounds of the present formula I are known compounds and are described in the literature. For example the synthesis of 1-methyl-2-phenylethynyl-1H-imidazole, 1-methyl-5-phenylethynyl-1H-imidazole and 1-methyl-4-phenylethynyl-1H-imidazole as well as the synthesis of the corresponding phenylethenyl derivatives is described in Chem. Pharm. Bull. 1987, 35(2), 823–828. The compounds have been prepared by palladium catalyzed reaction of corresponding halogen-1,3-azoles with phenylacetylene or styrene. 1-Methyl-2-(4-methoxy-phenylethynyl)-1H-imidazole can be synthesized as nonlinear optical chromophore according to Chem Mater. 1994, 6(7), 1023–1032. The preparation of 2-alkyl-5-phenylethynyl-1H-imidazole-4-carboxaldehydes as intermediates for the manufacture of substituted imidazoles for use as angiotensin II blockers has been described in WO 91/00277. 1-Methyl-5-(2-phenyl-ethenyl)-1H-imidazole has also been prepared as intermediate for the synthesis of heterocyclic food mutagens according to Environ. Health Perspect. 1986, 67, 41–45.

It has now surprisingly been found that compounds of formula I are metabotropic glutamate receptor antagonists having valuable therapeutic properties.

The present invention also relates to novel compounds of the formula

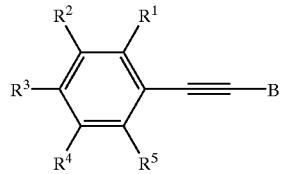

I-A wherein
- R¹, R², R³, R⁴ and R⁵ are independently selected from the group consising of, hydrogen, lower alkyl, —(CH₂)ₙ-halogen, lower alkoxy, —(CH₂)ₙ—NRR', —(CH₂)ₙ—N(R)—C(O)-lower alkyl, aryl, unsubstituted heteroaryl and heteroaryl substituted by one or more lower alkyl residues;
- R, R' and R" are selected from the group consisting hydrogen and lower alkyl;
- B is selected from the group consisting of

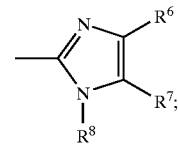

B1)

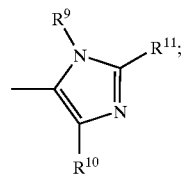

B2)

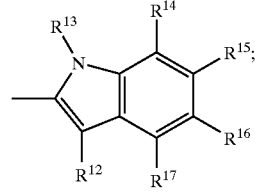

B3)

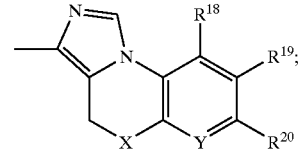

B4)

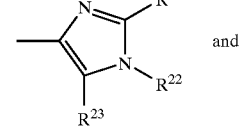

B5)

and

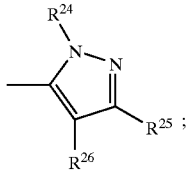

B6)

wherein
- $R^6$ is selected from the group consisting of hydrogen, lower alkyl, $-(CH_2)_n-C(O)OR$ and halogen;
- $R^7$ is selected from the group consisting of hydrogen, lower alkyl, $-(CH_2)_n-C(O)OR'$, halogen, nitro, unsubstituted heteroaryl and heteroaryl substituted by lower alkyl or cycloalkyl;
- $R^8$ is selected from the group consisting of hydrogen, lower alkyl, $-(CH_2)_n-OH$, $-(CH_2)_n-C(O)OR''$ and aryl;
- $R^9$ is lower alkyl;
- $R^{10}$ is selected from the group consisting of hydrogen, lower alkyl and halogen;
- $R^{11}$ is hydrogen or alkyl;
- $R^{12}$ is $-(CH_2)_n-N(R)-C(O)$-lower alkyl;
- $R^{13}$ is hydrogen or lower alkyl;
- $R^{14}, R^{15}, R^{16}$ and $R^{17}$ are independently selected from the group consisting of hydrogen, lower alkyl, $-(CH_2)_n$-halogen and lower alkoxy;
- $R^{18}, R^{19}$ and $R^{20}$ are independently selected from the group consisiting of hydrogen, lower alkyl, $-(CH_2)_n$-halogen or lower alkoxy;
- $R^{21}$ signifies hydrogen or lower alkyl;
- $R^{22}$ signifies hydrogen, lower alkyl or lower alkyl carrying at least one substituents selected from hydroxy and halogen;
- $R^{23}$ is selected from the group consisting of hydrogen, lower alkyl, lower alkanoyl and nitro;
- $R^{24}, R^{25}$ and $R^{26}$ are independently selected from the group consisting of hydrogen and lower alkyl;
- n is 0, 1, 2, 3, 4, 5 or 6;
- X is $-CH_2-$, $-O-$ or $-S-$; and
- Y is $-CH=$ or $-N=$;

and a pharmaceutically acceptable salt thereof; with the exception of
1-methyl-2-phenylethynyl-1H-imidazole,
1-methyl-2-(4-methoxy-phenylethynyl)-1H-imidazole,
1-methyl-5-phenylethynyl-1H-imidazole, and
1-methyl-4-phenylethynyl-1H-imidazole.

Furthermore, the present invention is a compound of the formula

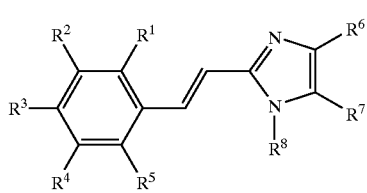

I-B-1 wherein
- $R^1, R^2, R^3, R^4$ and $R^5$ are independently selected from the group consisting of hydrogen, lower alkyl, $-(CH_2)_n$-halogen, lower alkoxy, $-(CH_2)_n-NRR'$, $-(CH_2)_n-N(R)-C(O)$-lower alkyl, aryl, unsubstitued heteroaryl and heteroaryl substituted by at least one lower alkyl-residues;
- R, R' and R" are hydrogen or lower alkyl;
- $R^6$ is selected from the group consisting of hydrogen, lower alkyl, $-(CH_2)_n-C(O)OR$ and halogen;
- $R^7$ is selected from the group consisting of hydrogen, lower alkyl, $-(CH_2)_n-C(O)OR'$, halogen, nitro, unsubstituted heteroaryl and heteroaryl substituted by lower alkyl or cycloalkyl; and
- $R^8$ signifies hydrogen, lower alkyl, $-(CH_2)_n-OH$, $-(CH_2)_n-C(O)OR''$ or aryl; or a pharmaceutically acceptable salt thereof.

The present invention also is a compound of formula

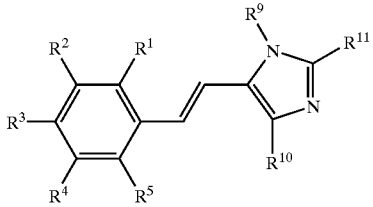

I-B-2 wherein
- $R^1, R^2, R^3, R^4$ and $R^5$ are independently selected from the group consisting of hydrogen, lower alkyl, $-(CH_2)_n$-halogen, lower alkoxy, $-(CH_2)_n-NRR'$, $-(CH_2)_n-N(R)-C(O)$-lower alkyl, aryl, unsubstituted heteroaryl and heteroaryl substituted by at least one lower alkyl;
- R and R' are independently selected from the group consisting of hydrogen and lower alkyl;
- $R^9$ is lower alkyl;
- $R^{10}$ is halogen; and
- $R^{11}$ is selected from the group hydrogen or alkyl;

or a pharmaceutically acceptable salt thereof.

DETAILED DESCRIPTION OF THE INVENTION

The following definitions of general terms used in the present description apply irrespective of whether the terms in question appear alone or in combination. The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "cycloalkyl" denotes a saturated carbocyclic group containing from 3 to 7 carbon atoms, preferred are cyclopropyl, cyclopentyl or cyclohexyl.

The term "halogen" denotes fluorine, chlorine, bromine and iodine.

The term "lower alkoxy" denotes a lower alkyl group as defined hereinbefore, which is bound via an oxygen atom, e.g. methoxy, ethoxy, n-propoxy, isopropoxy, n-butoxy and the like.

Preferred lower alkanoyl groups are formyl, ethanoyl or propanoyl.

Preferred aryl groups are phenyl or naphthyl. Heteroaryl groups are selected from furyl, pyrrolyl, thienyl, 1H-imidazolyl, 2H-imidazolyl, 4H-imidazolyl, 1H-pyrazolyl, 3H-pyrazolyl, 4H-pyrazolyl, 1,2-oxazolyl, 1,3-oxazolyl, 1H-[1,2,4]triazolyl, 4H-[1,2,4]triazolyl, 1H-[1,2,3]triazolyl, 2H-[1,2,3]triazolyl, 4H-[1,2,3]triazolyl, [1,2,4]oxadiazolyl, [1,3,4]oxadiazolyl, [1,2,3]oxadiazolyl, 1H-tetrazolyl, 2H-tetrazolyl, [1,2,3,4]oxatriazolyl, [1,2,3,5]oxatriazolyl, 1,3-thiazolyl, 1,2-thiazolyl, 1H-pentazolyl, pyridyl, pyrazinyl, pyrimidinyl, pyridazinyl, indolyl, quinolinyl and their dihydro derivatives. When the heteroaryl group is substituted, it is preferably subsituted by lower alkyl or cycloalkyl. Preferred heteroaryl groups are pyrrolyl and [1,2,4]oxadiazolyl, either substituted or unsubstituted.

The term "pharmaceutically acceptable salt" refers to any salt derived from an inorganic or organic acid or base which possesses the desired pharmacological activity of the parent compound.

Especially preferred are compounds of formula I for the above-mentioned method of treatment, in which A signifies —C≡C— and B signifies B1.

The following are examples of such compounds:
3,5-dimethyl-2-phenylethynyl-3H-imidazole-4-carboxylic acid ethyl ester,
5-methyl-2-phenylethynyl-3H-imidazole-4-carboxylic acid ethyl ester,
2-(3-methoxy-phenylethynyl)-3,5-dimethyl-3H-imidazole-4-carboxylic acid ethyl ester,
1-methyl-2-phenylethynyl-1H-imidazole,
2-(5-nitro-2-phenylethynyl-imidazol-1-yl)-ethanol,
2-phenylethynyl-1H-imidazole,
2-(2,6-dichloro-phenylethynyl)-3,5-dimethyl-3H-imidazole-4-carboxylic acid ethyl ester,
5-methyl-1-phenyl-2-phenylethynyl-1H-imidazole-4-carboxylic acid ethyl ester,
3,5-dimethyl-2-m-tolylethynyl-3H-imidazole-4-carboxylic acid ethyl ester,
2-(3-acetylamino-phenylethynyl)-3,5-dimethyl-3H-imidazole-4-carboxylic acid ethyl ester,
2-[3-(2,5-dimethyl-pyrrol-1-yl)-phenylethynyl]-3,5-dimethyl-3H-imidazole-4-carboxylic acid ethyl ester,
5-(3,5-dimethyl-2-phenylethynyl-3H-imidazol-4-yl)-3-methyl-[1,2,4]oxadiazole,
3-cyclopropyl-5-(3,5-dimethyl-2-phenylethynyl-3H-imidazol-4-yl)-[1,2,4]oxadiazole,
2-(4-chloro-phenylethynyl)-3,5-dimethyl-3H-imidazole-4-carboxylic acid ethyl ester,
2-(4-fluoro-phenylethynyl)-3,5-dimethyl-3H-imidazole-4-carboxylic acid ethyl ester,
2-biphenyl-4-ylethynyl-3,5-dimethyl-3H-imidazole-4-carboxylic acid ethyl ester,
2-(2-fluoro-phenylethynyl)-3,5-dimethyl-3H-imidazole-4-carboxylic acid ethyl ester,
2-(2-fluoro-phenylethynyl)-1-methyl-1H-imidazole,
2-(4-amino-phenylethynyl)-3,5-dimethyl-3H-imidazole-4-carboxylic acid ethyl ester,
2-(2-chloro-phenylethynyl)-1-methyl-1H-imidazole and
(4,5-dichloro-2-phenylethynyl-imidazol-1-yl)-acetic acid ethyl ester.

Further preferred are compounds of formula I for the above mentioned method of treatment, in which A signifies —C≡C— and B signifies B2.

An example for such a compound is 1-methyl-5-phenylethynyl-1H-imidazole.

Also preferred for the above mentioned method of treatment are compounds of formula I, in which A signifies —C≡C— and B signifies B3.

An example for such a compound is N—[2-(5-methoxy-2-phenylethynyl-1H-indol-3-yl)-ethyl]-acetamide.

Preferred compounds of formula I for the above mentioned method of treatment are also those, in which A signifies —C≡C— and B signifies B4.

The following are examples of such compounds:
3-phenylethynyl-4H-5-thia-2,6,9b-triaza-cyclopenta[a]naphthalene or
3-phenylethynyl-4H-5-oxa-2,9b-diaza-cyclopenta[a]naphthalene.

Further preferred are compounds of formula I for the above mentioned method of treatment, in which A signifies —C≡C— and B signifies B5.

Examples of such compounds are:
1-chloro-3-(2-methyl-5-nitro-4-phenylethynyl-imidazol-1-yl)-propan-2-ol,
3-methyl-5-phenylethynyl-3H-imidazole-4-carbaldehyde,
4-phenylethynyl-1H-imidazole,
1-methyl-4-phenylethynyl-1H-imidazole and
1,2-dimethyl-5-nitro-4-phenylethynyl-1H-imidazole.

Also preferred are compounds of formula I for the above mentioned method of treatment in which A signifies —C≡C— and B signifies B6.

An example for such a compound is 1,3-dimethyl-5-phenylethynyl-1H-pyrazole.

Further preferred are compounds of formula I for the above mentioned method of treatment, in which A signifies —C=C—.

Especially preferred are those compounds of formula I for the above mentioned method of treatment, in which A signifies —C=C— and B signifies B1.

The following are examples of such compounds:
4,5-diisopropyl-1-methyl-2-styryl-1H-imidazole,
2-[2-(4-fluoro-phenyl)-vinyl]-4,5-diisopropyl-1-methyl-1H-imidazole,
2-[2-(4-chloro-phenyl)-vinyl]-4,5-diisopropyl-1-methyl-1H-imidazole,
2-[2-(4-butoxy-phenyl)-vinyl]-4,5-diisopropyl-1-methyl-1H-imidazole,
4,5-diisopropyl-2-[2-(4-methoxy-2,3,6-trimethyl-phenyl)-vinyl]-1-methyl-1H-imidazole,
4,5-diisopropyl-2-[2-(4-methoxy-phenyl)-vinyl]-1-methyl-1H-imidazole,
2-[2-(4-chloro-3-fluoro-phenyl)-vinyl]-4,5-diisopropyl-1-methyl-1H-imidazole,
2-[2-(4-ethoxy-phenyl)-vinyl]-4,5-diisopropyl-1-methyl-1H-imidazole,
4,5-diisopropyl-1-methyl-2-[2-(2,3,4-trimethoxy-phenyl)-vinyl]-1H-imidazole,
2-[2-(2,4-dichloro-phenyl)-vinyl]-4,5-diisopropyl-1-methyl-1H-imidazole and
4,5-diisopropyl-1-methyl-2-(2-p-tolyl-vinyl)-1H-imidazole.

Also preferred are compounds of formula I for the above mentioned method of treatment, in which A signifies —C=C— and B signifies B2.

Examples of such compounds are the following:
4-bromo-1-methyl-5-styryl-1H-imidazole and
1-methyl-5-styryl-1H-imidazole.

Further preferred objects of the present invention are compounds of formula I-A, in which B signifies B1 with the exception of 1-methyl-2-phenylethynyl-1H-imidazole and 1-methyl-2-(4-methoxy-phenylethynyl)-1H-imidazole.

The following are examples of such compounds:
2-(5-nitro-2-phenylethynyl-imidazol-1-yl)-ethanol,
2-phenylethynyl-1H-imidazole,
2-(2-fluoro-phenylethynyl)-1-methyl-1H-imidazole,
2-(2-chloro-phenylethynyl)-1-methyl-1H-imidazole and
(4,5-dichloro-2-phenylethynyl-imidazol-1-yl)-acetic acid ethyl ester.

More preferred are compounds of formula I-A, in which B signifies B1 and $R^7$ is selected from the group consisting of $(CH_2)_n$—C(O)OR', unsubstituted heteroaryl and heteroaryl substituted by lower alkyl or cycloalkyl.

Especially preferred are those, in which $R^7$ signifies $(CH_2)_n$—C(O)OR', wherein n is 0 and R is lower alkyl.

Examples of such compounds are the following:

3,5-dimethyl-2-phenylethynyl-3H-imidazole-4-carboxylic acid ethyl ester,
5-methyl-2-phenylethynyl-3H-imidazole-4-carboxylic acid ethyl ester,
2-(3-methoxy-phenylethynyl)-3,5-dimethyl-3H-imidazole-4-carboxylic acid ethyl ester,
2-(2,6-dichloro-phenylethynyl)-3,5-dimethyl-3H-imidazole-4-carboxylic acid ethyl ester,
5-methyl-1-phenyl-2-phenylethynyl-1H-imidazole-4-carboxylic acid ethyl ester,
3,5-dimethyl-2-m-tolylethynyl-3H-imidazole-4-carboxylic acid ethyl ester,
2-(3-acetylamino-phenylethynyl)-3,5-dimethyl-3H-imidazole-4-carboxylic acid ethyl ester,
2-[3-(2,5-dimethyl-pyrrol-1-yl)-phenylethynyl]-3,5-dimethyl-3H-imidazole-4-carboxylic acid ethyl ester,
5-(3,5-dimethyl-2-phenylethynyl-3H-imidazol-4-yl)-3-methyl-[1,2,4]oxadiazole,
3-cyclopropyl-5-(3,5-dimethyl-2-phenylethynyl-3H-imidazol-4-yl)-[1,2,4]oxadiazole,
2-(4-chloro-phenylethynyl)-3,5-dimethyl-3H-imidazole-4-carboxylic acid ethyl ester,
2-(4-fluoro-phenylethynyl)-3,5-dimethyl-3H-imidazole-4-carboxylic acid ethyl ester,
2-biphenyl-4-ylethynyl-3,5-dimethyl-3H-imidazole-4-carboxylic acid ethyl ester,
2-(2-fluoro-phenylethynyl)-3,5-dimethyl-3H-imidazole-4-carboxylic acid ethyl ester, and
2-(4-amino-phenylethynyl)-3,5-dimethyl-3H-imidazole-4-carboxylic acid ethyl ester.

Also preferred are compounds of formula I-A, in which B signifies B4.

The following are examples of such compounds:
3-phenylethynyl-4H-5-thia-2,6,9b-triaza-cyclopenta[a]naphthalene and
3-phenylethynyl-4H-5-oxa-2,9b-diaza-cyclopenta[a]naphthalene.

Preferred compounds of formula I-A are also those, in which B signifies B5 with the exception of 1-methyl-4-phenylethynyl-1H-imidazole.

Examples of such compounds are the following:
1-chloro-3-(2-methyl-5-nitro-4-phenylethynyl-imidazol-1-yl)-propan-2-ol,
3-methyl-5-phenylethynyl-3H-imidazole-4-carbaldehyde,
4-phenylethynyl-1H-imidazole and
1,2-dimethyl-5-nitro-4-phenylethynyl-1H-imidazole.

Also preferred is a compound of formula

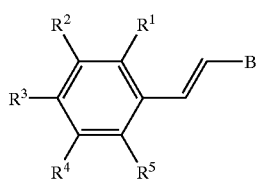

I-B wherein $R^1$, $R^2$, $R^3$, $R^4$ and $R^5$ are independently selected from the group consisting of each other, hydrogen, lower alkyl, —(CH$_2$)$_n$-halogen, lower alkoxy, —(CH$_2$)$_n$—NRR', —(CH$_2$)$_n$—N(R)—C(O)-lower alkyl, aryl, unsubstituted heteroaryl and heteroaryl substituted by at least one lower alkyl; and in which B signifies B1 and $R^7$ signifies lower alkyl or —(CH$_2$)$_n$—C(O)OR'.

Especially preferred are those in which $R^7$ is lower alkyl.

Examples of such compounds are the following:
4,5-diisopropyl-1-methyl-2-styryl-1H-imidazole,
2-[2-(4-fluoro-phenyl)-vinyl]-4,5-diisopropyl-1-methyl-1H-imidazole,
2-[2-(4-chloro-phenyl)-vinyl]-4,5-diisopropyl-1-methyl-1H-imidazole,
2-[2-(4-butoxy-phenyl)-vinyl]-4,5-diisopropyl-1-methyl-1H-imidazole,
4,5-diisopropyl-2-[2-(4-methoxy-2,3,6-trimethyl-phenyl)-vinyl]-1-methyl-1H-imidazole,
4,5-diisopropyl-2-[2-(4-methoxy-phenyl)-vinyl]-1-methyl-1H-imidazole,
2-[2-(4-chloro-3-fluoro-phenyl)-vinyl]-4,5-diisopropyl-1-methyl-1H-imidazole,
2-[2-(4-ethoxy-phenyl)-vinyl]-4,5-diisopropyl-1-methyl-1H-imidazole,
4,5-diisopropyl-1-methyl-2-[2-(2,3,4-trimethoxy-phenyl)-vinyl]-1H-imidazole,
2-[2-(2,4-dichloro-phenyl)-vinyl]-4,5-diisopropyl-1-methyl-1H-imidazole and
4,5-diisopropyl-1-methyl-2-(2-p-tolyl-vinyl)-1H-imidazole.

Further preferred compounds of formula I-B are those, in which B signifies B2 and $R^{10}$ is halogen.

An example of such a compound is 4-bromo-1-methyl-5-styryl-1H-imidazole.

The present compounds of formula I-A and I-B and their pharmaceutically acceptable salts can be prepared by methods known in the art, for example, by processes described below, which process comprises reacting a compound of the formula

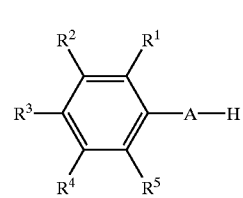

II with a compound of formula

B—X  III wherein X signifies halogen or trifluoromethanesulfonyl and $R^1$ to $R^5$ have the significances as defined before, to obtain a compound of formula I-A in the case if A signifies —C≡C— and B has the significances as defined before;

or to obtain a compound of formula I-B in the case if A signifies —HC=CH— and B is

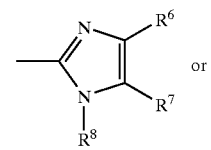

B1) or

B2)

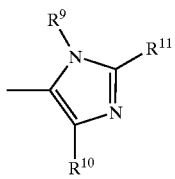

wherein

R⁶ is selected from the group consisting of hydrogen, lower alkyl, —(CH₂)ₙ—C(O)OR and halogen;

R⁷ is selected from the group consisting of hydrogen, lower alkyl, —(CH₂)ₙ—C(O)OR', halogen, nitro, or unsubstituted heteroaryl and heteroaryl substituted by lower alkyl or cycloalkyl;

R⁸ is selected from the group consisting of hydrogen, lower alkyl, —(CH₂)ₙ—OH, —(CH₂)ₙ—C(O)OR" and aryl;

R⁹ is lower alkyl;

R¹⁰ is halogen; and

R¹¹ is selected from the group hydrogen and alkyl;

and if desired, converting a compound of formulas I-A or I-B into a pharmaceutically acceptable salt.

This process is catalyzed by palladium(II) salts.

In accordance with the invention, compounds of formula I, wherein A signifies —C≡C—, are prepared by reacting an acetylene derivative of formula II, for example ethynylbenzene, with a suitable compound of formula III, for example 2-bromo-3,5-dimethyl-3H-imidazole-4-carboxylic acid ester. According to the method as described in Chem. Pharm. Bull. 1987, 35(2), 823–828 this palladium catalyzed C—C-coupling reaction requires the presence of bis(triphenylphosphine)-palladium(II)-chloride, cuprous iodide and triethylamine and is carried out in a polar solvent like dimethylformamide or acetonitrile at a temperature of 90° C. to 100° C. within 1.5 to 3 hours. The reaction can also be carried out in the presence equimolar amounts of bis (triphenylphosphine)-palladium(II)-chloride and triphenylphosphine and an excess of triethylamine at a temperature of 55° C. within 16 hours.

The phenylethynyl derivatives of formula II are commercially available or can be easily prepared by methods well known in the art.

The compounds of formula III are also commercially available or can be prepared by appropiate methods depending on the heterocyclic system B.

2-Halogeno-1H-imidazoles of formula III (B=B1) are prepared according to methods as described in U.S. Pat. Nos. 4,711,962, 3,341,548 and Synth. Commun. 1989, 19, 2551–2566.

2-Trifluoromethanesulfonyl-1H-imidazoles of formula IIIa can be prepared from a 2-oxo-2,3-dihydro-1H-imidazole of formula VI, for example from 5-methyl-2-oxo-1-phenyl-2,3-dihydro-1H-imidazole-4-carboxylic acid ethyl ester which is obtained according to the method as described in U.S. Pat. No. 3,303,199. The reaction with trifluoromethanesulfonic anhydride and triethylamine is carried out in dichloromethane at room temperature (Scheme 1, Tf=trifluoromethanesulfonyl).

Scheme 1

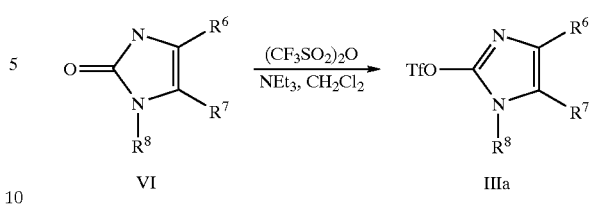

5-(2-Bromo-3,5-dimethyl-3H-imidazol-4-yl)-[1,2,4] oxadiazoles of formula IIIb are obtained by reacting 3,5-dimethyl-3H-imidazole-4-carboxylic acid VII with N-hydroxy-carboxamidines of formula VIII in the presence of 1,1'-carbonyldiimidazole and dimethyl-formamide as solvent to give imidazolyl-[1,2,4]oxadiazoles of formula IX which are then brominated at room temperature (Scheme 2, R" is lower alkyl or cycloalkyl).

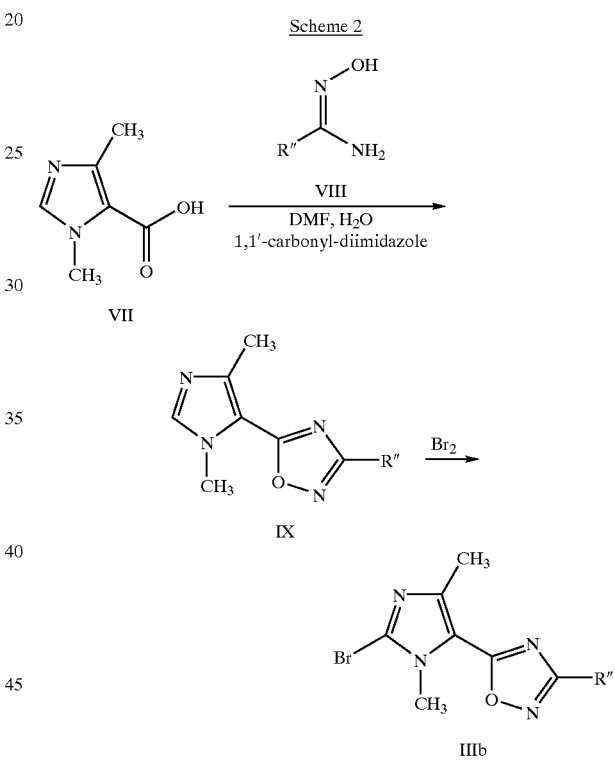

A suitable indole derivative of formula III (B=B3), for example N-[2-(2-iodo-5-methoxy-1H-indol-3-yl)-ethyl]-actamide, can be obtained in accordance with the method as described in J. Labelled Compd. Radiopharm. 1997, 39, 677–684.

3-Iodo-4H-5-thia-2,6,9b-triaza-cyclopenta[a]naphtalenes and 3-iodo-4H-5-oxa-2,9b-diaza-cyclopenta[a]naphthalenes of formula III (B=B4) are prepared in analogy to the method as described in EP 0 059 390.

4-Halogeno-1H-imidazoles of formula III (B=B5) can be obtained according to methods as described for example in J. Med. Chem. 1974, 17(9), 1019–1020, Chem. Pharm. Bull. 1994, 42, 1784–1790 or Aust. J. Chem. 1987, 40(8), 1399–1413.

Compounds of formula III, in which B signifies B6, can be prepared for example in analogy to a method described in Bull. Acad. Sci. USSR Div. Chem. Sci. (Engl. Transl.) 1983, 626–628 and in Izv. Akad. Nauk SSSR Ser. Khim. 1983, 688–690.

Phenylethenyl derivatives of formula I can be prepared analogously by reacting a compound of formula III with a phenylethene of formula II.

Furthermore, compounds of formula I, in which A signifies —C≡C—, and their pharmaceutically acceptable salts can also be obtained by reacting a compound of the formula

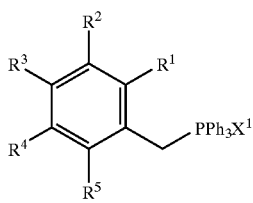

IV wherein $X^1$ is halogen, with a compound of the formula

V to obtain a compound of formula

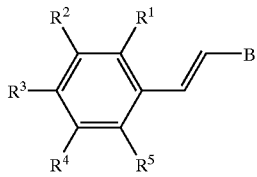

I-B wherein $R^1$ to $R^5$ are as described above and B is

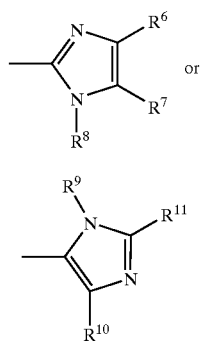

B1)

or

B2)

wherein
R$^6$ is selected from the group consisting of hydrogen, lower alkyl, —(CH$_2$)$_n$—C(O)OR and halogen;
R$^7$ is selected from the group consisting of hydrogen, lower alkyl, —(CH$_2$)$_n$—C(O)OR', halogen, nitro, unsubstituted heteroaryl unsubstituted and heteroaryl substituted by lower alkyl or cycloalkyl;
R$^8$ is selected from the group consisting of hydrogen, lower alkyl, —(CH$_2$)$_n$—OH, —(CH$_2$)$_n$—C(O)OR'' and aryl;
R$^9$ is lower alkyl;
R$^{10}$ is halogen; and
R$^{11}$ is selected from the group consisting of hydrogen or alkyl;

and converting a compound of formula I-B into a pharmaceutically acceptable salt.

Thus, compounds of formula I-B are obtained in a Wittig reaction by treating an appropiate aldehyde of formula V, for example 4,5-diisopropyl-1-methyl-1H-imidazole-2-carbaldehyde, with a suitable benzyltripheylphosphonium halide of formula IV, for example benzyltriphenylphosphoniumchloride in the presence of a strong base like a sodium alkoxide, sodium amide or sodium hydride.

Triphenylphosphonium salts of formula IV are prepared from triphenylphosphine (PPh$_3$) and the appropiate benzyl halides X (Scheme 3).

Scheme 3

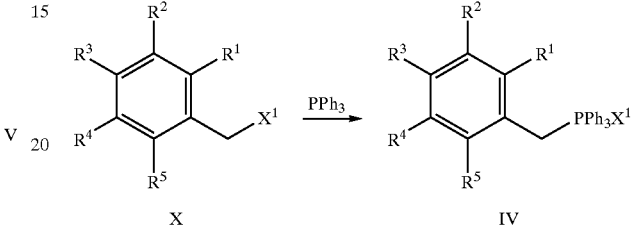

X                    IV

Aldehydes of formula V can be obtained by methods known in the art. For example, 4,5-diisopropyl-1-methyl-1H-imidazole-2-carbaldehyde is prepared in analogy with a method as described in Inorg. Chim. Acta 1999, 296 (1), 208–221, and 5-bromo-3-methyl-3H-imidazole-4-carbaldehyde is obtained in accordance to a method as described in Chem. Pharm. Bull. 1994, 42, 1784–1790.

The pharmaceutically acceptable salts of compounds of formula I-A and I-B can be manufactured readily according to methods known to those skilled in the art taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of all of the example compounds was tested using the following method:

cDNA encoding rat mGlu 5a receptor was transiently transfected into EBNA cells using a procedure described by E.-J. Schlaeger and K. Christensen (Transient gene expression in mammalian cells grown in serum-free suspension culture; Cytotechnology, 30: 71–83,1999). [$Ca^{2+}$]i measurements were performed on mGlu 5a transfected EBNA cells after incubation of the cells with Fluo 3-AM (obtainable by FLUKA, 0.5 µM final concentration) for 1 hour at 37° C. followed by 4 washes with assay buffer (DMEM supplemented with Hank's salt and 20 mM HEPES. [$Ca^{2+}$]i measurements were done using a fluorometric imaging plate reader (FLIPR, Molecular Devices Corporation, La Jolla, Calif., USA). When compounds were evaluated as antagonists they were tested against 10 µM glutamate as agonist.

The inhibition (antagonists) curves were fitted with a four parameter logistic equation giving $IC_{50}$, and Hill coefficient using the iterative non linear curve fitting software Origin (Microcal Software Inc., Northampton, Mass., USA).

The compounds of the present invention are mGluR 5a receptor antagonists. The compounds show activities, as measured in the assay described above, of 10 µM or less, typically 2 µM or less, and preferably of 0.02 µM or less.

The Table I below are shown specific activity data of the compounds of the present invention derived according to the procedure described above:

TABLE I

| Example No. | Compound name | $IC_{50}$ (µM) |
|---|---|---|
| 1 | 3,5-dimethyl-2-phenylethynyl-3H-imidazole-4-carboxylic acid ethyl ester | 0.25 |
| 2 | 5-methyl-2-phenylethynyl-3H-imidazole-4-carboxylic acid ethyl ester | 2.40 |
| 3 | 2-(3-methoxy-phenylethynyl)-3,5-dimethyl-3H-imidazole-4-carboxylic acid ethyl ester | 0.35 |
| 4 | 1-methyl-2-phenylethynyl-1H-imidazole | 0.72 |
| 5 | 2-(5-nitro-2-phenylethynyl-imidazol-1-yl)-ethanol | 2.11 |
| 6 | 2-phenylethynyl-1H-imidazole | 0.20 |
| 7 | 2-(2,6-dichloro-phenylethynyl)-3,5-dimethyl-3H-imidazole-4-carboxylic acid ethyl ester | 10 |
| 8 | 5-methyl-1-phenyl-2-phenylethynyl-1H-imidazole-4-carboxylic acid ethyl ester | <10 |
| 9 | 3,5-dimethyl-2-m-tolylethynyl-3H-imidazole-4-carboxylic acid ethyl ester | 0.13 |
| 10 | 2-(3-acetylamino-phenylethynyl)-3,5-dimethyl-3H-imidazole-4-carboxylic acid ethyl ester | 2.12 |
| 11 | (2-[3-(2,5-dimethyl-pyrrol-1-yl)-phenylethynyl]-3,5-dimethyl-3H-imidazole-4-carboxylic acid ethyl ester | 0.18 |
| 12 | 5-(3,5-dimethyl-2-phenylethynyl-3H-imidazol-4-yl)-3-methyl-[1,2,4]oxadiazole | 0.011 |
| 14 | 2-(4-chloro-phenylethynyl)-3,5-dimethyl-3H-imidazole-4-carboxylic acid ethyl ester | <10 |
| 15 | 2-(4-fluoro-phenylethynyl)-3,5-dimethyl-3H-imidazole-4-carboxylic acid ethyl ester | 0.25 |
| 16 | 2-biphenyl-4-ylethynyl-3,5-dimethyl-3H-imidazole-4-carboxylic acid ethyl ester | 0.21 |

TABLE I-continued

| Example No. | Compound name | $IC_{50}$ (µM) |
|---|---|---|
| 17 | 2-(2-fluoro-phenylethynyl)-3,5-dimethyl-3H-imidazole-4-carboxylic acid ethyl ester | 0.09 |
| 18 | 2-(2-fluoro-phenylethynyl)-1-methyl-1H-imidazole | 0.07 |
| 19 | 2-(4-amino-phenylethynyl)-3,5-dimethyl-3H-imidazole-4-carboxylic acid ethyl ester | 1.53 |
| 20 | 2-(2-chloro-phenylethynyl)-1-methyl-1H-imidazole | 1.10 |
| 21 | (4,5-dichloro-2-phenylethynyl-imidazol-1-yl)-acetic acid ethyl ester | 0.52 |
| 22 | 1-methyl-5-phenylethynyl-1H-imidazole | 0.22 |
| 23 | N-[2-(5-methoxy-2-phenylethynyl-1H-indol-3-yl)-ethyl]-acetamide | 0.58 |
| 24 | 3-phenylethynyl-4H-5-thia-2,6,9b-triaza-cyclopenta[a]naphthalene | 0.15 |
| 25 | 3-phenylethynyl-4H-5-oxa-2,9b-diaza-cyclopenta[a]naphthalene | 0.07 |
| 26 | 1-chloro-3-(2-methyl-5-nitro-4-phenylethynyl-imidazol-1-yl)-propan-2-ol | 0.23 |
| 27 | 3-methyl-5-phenylethynyl-3H-imidazole-4-carbaldehyde | 1.79 |
| 28 | 4-phenylethynyl-1H-imidazole | 3.36 |
| 29 | 1-methyl-4-phenylethynyl-1H-imidazole | 0.50 |
| 30 | 1,2-dimethyl-5-nitro-4-phenylethynyl-1H-imidazole | 0.02 |
| 31 | 1,3-dimethyl-5-phenylethynyl-1H-pyrazole | 5–10 |
| 32 | 4,5-diisopropyl-1-methyl-2-styryl-1H-imidazole | 1.82 |
| 33 | 2-[2-(4-fluoro-phenyl)-vinyl]-4,5-diisopropyl-1-methyl-1H-imidazole | 5–10 |
| 34 | 2-[2-(4-chloro-phenyl)-vinyl]-4,5-diisopropyl-1-methyl-1H-imidazole | 5–10 |
| 35 | 2-[2-(4-butoxy-phenyl)-vinyl]-4,5-diisopropyl-1-methyl-1H-imidazole | 5–10 |
| 36 | 4,5-diisopropyl-2-[2-(4-methoxy-2,3,6-trimethyl-phenyl)-vinyl]-1-methyl-1H-imidazole | 5–10 |
| 37 | 4,5-diisopropyl-2-[2-(4-methoxy-phenyl)-vinyl]-1-methyl-1H-imidazole | 5–10 |
| 38 | 2-[2-(4-chloro-3-fluoro-phenyl)-vinyl[-4,5-diisopropyl-1-methyl-1H-imidazole | 10 |
| 39 | 2-[2-(4-ethoxy-phenyl)-vinyl]-4,5-diisopropyl-1-methyl-1H-imidazole | 10 |
| 40 | 4,5-diisopropyl-1-methyl-2-[2-(2,3,4-trimethoxy-phenyl)-vinyl[-1H-imidazole | 10 |
| 41 | 2-[2-(2,4-dichloro-phenyl)-vinyl]-4,5-diisopropyl-1-methyl-1H-imidazole | 10 |
| 42 | 4,5-diisopropyl-1-methyl-2-(2-p-tolyl-vinyl)-1H-imidazole | 3.25 |
| 43 | 4-bromo-1-methyl-5-styryl-1H-imidazole | 3.06 |
| 44 | 1-methyl-5-styryl-1H-imidazole | 8.0 |

The compounds of formula I and pharmaceutically acceptable salts thereof can be used as pharmaceutical compositions, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a therapeutically effective amount of compound of formula IA or IB or pharmaceutically acceptable salts thereof and a therapeutically inert excipient are also an object of the present invention, as is a process for the production of such pharmaceutical compositions which comprises bringing one or more compounds of formula IA or IB or pharmaceutically acceptable salts thereof and, if desired, one or more other therapeutically valuable substances into a galenical dosage form together with one or more therapeutically inert carriers.

The dosage can vary within wide limits and will, of course, be adapted to the individual requirements in each particular case. In general, the effective dosage for oral or parenteral administration is between 0.01–20 mg/kg/day, with a dosage of 0.1–10 mg/ kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of pharmaceutical compositions, especially for the for the treatment or prevention of mGluR5 receptor mediated disorders of the aforementioned kind, is also an object of the invention.

The following examples are provided for illustration of the invention. They should not be considered as limiting the scope of the invention, but merely as being representative thereof.

EXAMPLE 1

3,5-Dimethyl-2-phenylethynyl-3H-imidazole-4-carboxylic acid ethyl ester a) 2-Bromo-3,5-dimethyl-3H-imidazole-4-carboxylic acid ethyl ester The title compound was prepared according to the method as described in U.S. Pat. No. 4,711,962.

b) 3,5-Dimethyl-2-phenylethynyl-3H-imidazole-4-carboxylic acid ethyl ester

In analogy to the method as described in Chem. Pharm. Bull. 1987, 35(2), 823–828, 17.5 mg (0.025 mmol) bis-(triphenylphosphine)-palladium-II-chloride, 2.9 mg (0.015 mmol) cuprous iodide, 60.5 mg (0.6 mmol) triethylamine, 32.4 mg (0.3 mmol) ethynylbenzene and 61.8 mg (0.25 mmol) 2-bromo-3,5-dimethyl-3H-imidazole-4-carboxylic acid ethyl ester are dissolved in 1 ml DMF and shaken for 3 h at 90° C. The title compound (19.3 mg, 29%, MS: m/e=269.3, [M+H$^+$]) was isolated from the reaction mixture by HPLC chromatography (YMC CombiPrep C18 column 50×20 mm, solvent gradient 10–95% CH$_3$CN in 0.1% TFA(aq) over 6.0 min, λ=230 nm, flow rate 40 ml/min).

$^1$H-NMR (400 MHz, CDCl$_3$, 25° C.): δ (ppm)=1.39 (3H, t, J=7.22 Hz), 2.51 (3H, s), 3.99 (3H, s), 4.35 (2H, q, J=7.22 Hz), 7.34–7.40 (3H, m), 7.56–7.59 (2H, m).

$^{13}$C-NMR (100 MHz, CDCl$_3$, 25° C.): δ (ppm)=14.26, 15.78, 34.31, 60.44, 77.83, 94.86, 119.77, 121.14, 128.46, 129.48, 131.82, 134.55, 147.76, 160.58.

EXAMPLE 2

5-Methyl-2-phenylethynyl-3H-imidazole-4-carboxylic acid ethyl ester a) 2-Bromo-5-methyl-3H-imidazole-4-carboxylic acid ethyl ester The compound was prepared according to the method described in U.S. Pat. No. 4,711,962.

b) 5-Methyl-2-phenylethynyl-3H-imidazole-4-carboxylic acid ethyl ester

The title compound, MS: m/e=255.2 (M+H$^+$) was prepared in accordance with the general method of example 1b from 2-bromo-5-methyl-3H-imidazole-4-carboxylic acid ethyl ester.

EXAMPLE 3

2-(3-Methoxy-phenylethynyl)-3,5-dimethyl-3H-imidazole-4-carboxylic acid ethyl ester The title compound, MS: m/e=299.3 (M+H$^+$) was prepared in accordance with the general method of example 1b from 2-bromo-3,5-dimethyl-3H-imidazole-4-carboxylic acid ethyl ester and 1-ethynyl-3-methoxy-benzene.

EXAMPLE 4

1-Methyl-2-phenylethynyl-1H-imidazole

The title compound, MS: m/e=183.0 (M+H$^+$) was prepared in accordance with the general method of example 1b from 2-iodo-1-methyl-1H-imidazole.

EXAMPLE 5

2-(5-Nitro-2-phenylethynyl-imidazol-1-yl)-ethanol a) 2-(2-Iodo-5-nitro-imidazol-1-yl)-ethanol 2-(2-Iodo-5-nitro-imidazol-1-yl)-ethanol was obtained in accordance with the method as described in U.S. Pat. No. 3,341,548.

b) 2-(5-Nitro-2-phenylethynyl-imidazol-1-yl)-ethanol

The title compound, MS: m/e=258.0 (M+H$^+$) was prepared in accordance with the general method of example 1b from 2-(2-iodo-5-nitro-imidazol-1-yl)-ethanol.

EXAMPLE 6

2-Phenylethynyl-1H-imidazole a) 2-Iodoimidazole

2-Iodoimidazole was prepared in accordance with the method as described in Synth. Commun. 1989, 19, 2551–2566.

b) 2-Phenylethynyl-1H-imidazole

The title compound, MS: m/e=169.4 (M+H$^+$) was prepared in accordance with the general method of example 1b from 2-iodoimidazole.

EXAMPLE 7

2-(2,6-Dichloro-phenylethynyl)-3,5-dimethyl-3H-imidazole-4-carboxylic acid ethyl ester The title compound, MS: m/e=197.4 (M+H$^+$) was prepared in accordance with the general method of example 1b from 1,3-dichloro-2-ethynyl-benzene and 2-bromo-3,5-dimethyl-3H-imidazole-4-carboxylic acid ethyl ester.

EXAMPLE 8

5-Methyl-1-phenyl-2-phenylethynyl-1H-imidazole-4-carboxylic acid ethyl ester a) 5-Methyl-2-oxo-1-phenyl-2,3-dihydro-1H-imidazole-4-carboxylic acid ethyl ester The title compound was obtained by the method as described in U.S. Pat. No. 3,303,199.

b) 5-Methyl-1-phenyl-2-phenylethynyl-1H-imidazole-4-carboxylic acid ethyl ester

A mixture of 492 mg (2 mmol) 5-methyl-2-oxo-1-phenyl-2,3-dihydro-1H-imidazole-4-carboxylic acid ethyl ester, 846 mg (3 mmol) trifluoromethanesulfonic anhydride, 303 mg (3 mmol) triethylamine and 10 ml dichloromethane was stirred for 1 h at room temperature. The volatile components were evaporated under reduced pressure and the obtained residue was filtered over silica gel (ethyl acetate/hexane=1:4 as eluent). After evaporation of the solvent under reduced pressure, a yellow oil (463 mg) was obtained. 378 mg of this oil, 122 mg (1.2 mmol) Phenylacetylene, 70 mg (0.1 mmol) bis-(triphenylphosphine)-palladium-II-chloride, 303 mg (3 mmol) triethylamine, and 10 mg (0.05 mmol) of cuprous iodide were dissolved in 5 ml DMF and stirred for 1.5 h at 100° C. The reaction mixture was cooled to room temperature, diluted with 30 ml ether, washed with water and brine and dried over $MgSO_4$. Evaporation of the solvent gave an oil from which the title compound (277 mg, 51%) was isolated by column chromatography (silica gel, Ethyl acetate/Hexane=2:3 as eluant).

$^1$H-NMR (400 MHz, $CDCl_3$, 25° C.): δ (ppm)=1.44 (3H, t, J=7 Hz), 2.47 (3H, s), 4.42 (2H, q, J=7Hz), 7.20–7.42 (5H, m), 7.34–7.38 (2H, m), 7.53–7.60 (3H, m).

$^{13}$C-NMR (100 MHz, $CDCl_3$, 25° C.): δ (ppm)=11.53, 14.94, 60.90, 79.34, 92.92, 121.91, 127.79, 128.73, 129.47, 129.86, 130.00, 130.15, 131.90, 132.08, 135,42, 137.91, 163.75.

EXAMPLE 9

3,5-Dimethyl-2-m-tolylethynyl-3H-imidazole-4-carboxylic acid ethyl ester

The title compound, MS: m/e=283.6 (M+H$^+$), was prepared in accordance with the general method of example 1b from 1-ethynyl-3-methyl-benzene and 2-bromo-3,5-dimethyl-3H-imidazole-4-carboxylic acid ethyl ester.

EXAMPLE 10

2-(3-Acetylamino-phenylethynyl)-3,5-dimethyl-3H-imidazole-4-carboxylic acid ethyl ester The title compound, MS: m/e=326.8 (M+H$^+$), was prepared in accordance with the general method of example 1b from N-(3-ethynyl-phenyl)-acetamide and 2-bromo-3,5-dimethyl-3H-imidazole-4-carboxylic acid ethyl ester.

EXAMPLE 11

(2-[3-(2,5-Dimethyl-pyrrol-1-yl)-phenylethynyl]-3,5-dimethyl-3H-imidazole-4-carboxylic acid ethyl ester The title compound, MS: m/e=362.8 (M+H$^+$), was prepared in accordance with the general method of example 1b from 2-bromo-3,5-dimethyl-3H-imidazole-4-carboxylic acid ethyl ester and 1-(3-ethynyl-phenyl)-2,5-dimethyl-1H-pyrrole.

EXAMPLE 12

5-(3,5-Dimethyl-2-phenylethynyl-3H-imidazol-4-yl)-3-methyl-[1,2,4]oxadiazole a) 5-(3,5-Dimethyl-3H-imidazol-4-yl)-3-methyl-[1,2,4]oxadiazole A solution of 3,5-dimethyl-3H-imidazole-4-carboxylic acid (1.0 g, 7.14 mmol) and 1,1'-carbonyldiimidazole (1.74 g, 10.7 mmol) in DMF (35 ml) was stirred at RT for 3 h. N-hydroxy-acetamidine (0.68 g, 9.18 mmol) was added, the reaction mixture was stirred at 16 h at 80° C., evaporated and dissolved in acetic acid (30 ml). The solution was stirred at 100° C. for 2 h, evaporated, poured into sat. $NaHCO_3$ solution (50 ml) and extracted with dichloromethane (7×30 ml). The combined organic layers were washed with brine (70 ml), dried ($MgSO_4$) and evaporated to give the title compound (0.78 g, 61%) as a white solid, m.p. 95° C. and MS: m/e=178.2 (M$^+$).

b) 5-(2-Bromo-3,5-dimethyl-3H-imidazol-4-yl)-3-methyl-[1,2,4]oxadiazole

To a stirred solution of 5-(3,5-dimethyl-3H-imidazol-4-yl)-3-methyl-[1,2,4]oxadiazol (0.7 g, 3.93 mmol) in chloroform (7 ml) was added dropwise at RT a solution of bromine (0.94 g; 0.30 ml, 5.89 mmol) in chloroform (7 ml). The reaction mixture was stirred at RT for 26 h, evaporated, poured into sat. $NaHCO_3$ solution (40 ml) and extracted with dichloromethane (2×30 ml). The combined organic layers were washed with brine (40 ml), dried ($MgSO_4$) and evaporated to give the crude product as yellow oil (0.84 g). Purification by column chromatography on silica gel (ethyl acetate/MeOH 98:2) gave the title compound (0.52 g, 51%) as a white solid, m.p. 89° C. and MS: m/e=256, 258 (M$^+$).

c) 5-(3,5-Dimethyl-2-phenylethynyl-3H-imidazol-4-yl)-3-methyl-[1,2,4]oxadiazole

To a stirred solution of 5-(2-bromo-3,5-dimethyl-3H-imidazol-4-yl)-3-methyl-[1,2,4]oxadiazole (0.52 g, 2.02 mmol) in THF (10 mmol) was added at RT bis(triphenylphosphin)palladium(II)chloride (71 mg, 0.1 mmol), phenylacetylene (0.31 g, 3.03 mmol), triphenylphosphine (27 mg, 0.1 mmol) and triethylamine (0.61 g, 6.07 mmol). Through the reaction mixture was bubbled argon for 10 min and stirring was continued at 55° C. for 16 h. The reaction mixture was poured into water (50 ml) and extracted with ethyl acetate (2×50 ml). The combined organic layers were washed with brine (40 ml), dried ($MgSO_4$) and evaporated to give the crude product as yellow oil (0.81 g). Purification by column chromatography on silica gel (ethyl acetate/toluene 5:1) gave the title compound (0.31 g, 55%) as a light yellow solid, m.p. 137° C. and MS: m/e=278.1 (M$^+$).

EXAMPLE 13

3-Cyclopropyl-5-(3,5-dimethyl-2-phenylethynyl-3H-imidazol-4-yl)-[1,2,4]oxadiazole a) 3-Cyclopropyl-5-(3,5-dimethyl-3H-imidazol-4-yl)-[1,2,4]oxadiazole The title compound, off-white solid, m.p. 88° C. and MS: m/e=204.3 (M$^+$), was prepared from 3,5-dimethyl-3H-imidazole-4-carboxylic acid and N-hydroxy-cyclopropanecarboxamidine in accordance with the general procedure of example 12a.

b) 5-(2-Bromo-3,5-dimethyl-3H-imidazol-4-yl)-3-cyclopropyl-[1,2,4]oxadiazole

The title compound, white solid, m.p. 81° C. and MS: m/e=282, 284 (M$^+$), was prepared by bromination of 3-cyclopropyl-5-(3,5-dimethyl-3H-imidazol-4-yl)-[1,2,4]oxadiazole in accordance with the general method of example 12b.

c) 3-Cyclopropyl-5-(3,5-dimethyl-2-phenylethynyl-3H-imidazol-4-yl)-[1,2,4]oxadiazole The title compound, white solid, m.p. 120° C. and MS: m/e=305.2 (M+H$^+$), was prepared from 5-(2-bromo-3,5-dimethyl-3H-imidazol-4-yl)-3-cyclopropyl-[1,2,4]oxadiazole and phenylacetylene in accordance with the general procedure of example 12c.

EXAMPLE 14

2-(4-Chloro-phenylethynyl)-3,5-dimethyl-3H-imidazole-4-carboxylic acid ethyl ester The title compound, MS: m/e=303.0 (M+H$^+$) was prepared in accordance with the general method of example 1b from 2-bromo-3,5-dimethyl-3H-imidazole-4-carboxylic acid ethyl ester and 1-chloro-4-ethynylene.

EXAMPLE 15

2-(4-Fluoro-phenylethynyl)-3,5-dimethyl-3H-imidazole-4-carboxylic acid ethyl ester The title compound, MS: m/e=286.8 (M+H$^+$) was prepared in accordance with the general method of example 1b from 2-bromo-3,5-dimethyl-3H-imidazole-4-carboxylic acid ethyl ester and 1-ethynyl-4-fluorobenzene.

EXAMPLE 16

2-Biphenyl-4-ylethynyl-3,5-dimethyl-3H-imidazole-4-carboxylic acid ethyl ester

The title compound, MS: m/e=345.4 (M+H$^+$) was prepared in accordance with the general method of example 1b from 2-bromo-3,5-dimethyl-3H-imidazole-4-carboxylic acid ethyl ester and 4-ethynylbiphenyl.

EXAMPLE 17

2-(2-Fluoro-phenylethynyl)-3,5-dimethyl-3H-imidazole-4-carboxylic acid ethyl ester The title compound, MS: m/e=287.4 (M+H$^+$) was prepared in accordance with the general method of example 1b from 2-bromo-3,5-dimethyl-3H-imidazole-4-carboxylic acid ethyl ester and 1-ethynyl-2-fluorobenzene.

EXAMPLE 18

2-(2-Fluoro-phenylethynyl)-1-methyl-1H-imidazole

The title compound, MS: m/e=201.2 (M+H$^+$) was prepared in accordance with the general method of example 1b from 2-iodo-1-methyl-1H-imidazole and 1-ethynyl-2-fluorobenzene.

EXAMPLE 19

2-(4-Amino-phenylethynyl)-3,5-dimethyl-3H-imidazole-4-carboxylic acid ethyl ester The title compound, MS: m/e=284.4 (M+H$^+$) was prepared in accordance with the general method of example 1b from 2-bromo-3,5-dimethyl-3H-imidazole-4-carboxylic acid ethyl ester and 4-ethynylaniline.

EXAMPLE 20

2-(2-Chloro-phenylethynyl)-1-methyl-1H-imidazole

The title compound, MS: m/e=217.6 (M+H$^+$) was obtained in accordance with the general method of example 1b from 2-iodo-1-methyl-1H-imidazole and 1-chloro-2-ethynylbenzene.

EXAMPLE 21

(4,5-Dichloro-2-phenylethynyl-imidazol-1-yl)-acetic acid ethyl ester

The title compound, MS: m/e=323.0 (M+H$^+$) was prepared in accordance with the general method of example 1b from ethyl (2-bromo-4,5-dichloroimidazole-1-yl) acetate and ethynylbenzene.

EXAMPLE 22

1-Methyl-5-phenylethynyl-1H-imidazole

The title compound, MS: m/e=183.4(M+H$^+$) was prepared in accordance with the general method of example 1b from 5-iodo-1-methyl-1H-imidazole.

EXAMPLE 23

N-[2-(5-Methoxy-2-phenylethynyl-1H-indol-3-yl)-ethyl]-acetamide a) N-[2-(2-iodo-5-methoxy-1H-indol-3-yl)-ethyl]-acetamide The title compound is obtained from N-[2-(5-methoxy-indol-3-yl)-ethyl]-acetamide according to the method as described in J. Labelled Compd. Radiopharm. 1997, 39, 677–684.

b) N-[2-(5-Methoxy-2-phenylethynyl-1H-indol-3-yl)-ethyl]-acetamide

The title compound, MS: m/e=333.3 (M+H$^+$) was prepared in accordance with the general method of example 1b from N-[2-(2-iodo-5-methoxy-1H-indol-3-yl)-ethyl]-acetamide.

EXAMPLE 24

3-Phenylethynyl-4H-5-thia-2,6,9b-triaza-cyclopenta[a]naphthalene a) 3-Iodo-4H-5-thia-2,6,9b-triaza-cyclopenta[a]naphthalene In analogy to the method as described in EP 0 059 390 the title compound was obtained.

b) 3-Phenylethynyl-4H-5-thia-2,6,9b-triaza-cyclopenta[a]naphthalene

The title compound, MS: m/e=290.3 (M+H$^+$) was prepared in accordance with the general method of example 1b from 3-iodo-4H-5-thia-2,6,9b-triaza-cyclopenta[a]naphthalene.

EXAMPLE 25

3-Phenylethynyl-4H-5-oxa-2,9b-diaza-cyclopenta[a]naphthalene a) 3-Iodo-4H-5-oxa-2,9b-diaza-cyclopenta[a]naphthalene 3-Iodo-4H-5-oxa-2,9b-diaza-cyclopenta[a]naphthalene was obtained in analogy to the method as described EP 0 059 390.

b) 3-Phenylethynyl-4H-5-oxa-2,9b-diaza-cyclopenta[a]naphthalene

The title compound, MS: m/e=273.2 (M+H$^+$), 545.1 (2M+H$^+$), was prepared in accordance with the general method of example 1b from 3-iodo-4H-5-oxa-2,9b-diaza-cyclopenta[a]naphthalene.

EXAMPLE 26

1-Chloro-3-(2-methyl-5-nitro-4-phenylethynyl-imidazol-1-yl)-propan-2-ol a) 1-Chloro-3-(4-iodo-2-methyl-5-nitro-imidazol-1-yl)-propan-2-ol 1-Chloro-3-(4-iodo-2-methyl-5-nitro-imidazol-1-yl)-propan-2-ol was obtained by the method as described in J. Med. Chem. 1974, 17(9), 1019–20.

b) 1-Chloro-3-(2-methyl-5-nitro-4-phenylethynyl-imidazol-1-yl)-propan-2-ol

The title compound, MS: m/e=319.7, 321.9 (M+H$^+$) was prepared in accordance with the general method of example 1b from 1-chloro-3-(4-iodo-2-methyl-5-nitro-imidazol-1-yl)-propan-2-ol.

EXAMPLE 27

3-Methyl-5-phenylethynyl-3H-imidazole-4-carbaldehyde a) 5-Bromo-3-methyl-3H-imidazole-4-carbaldehyde 5-Bromo-3-methyl-3H-imidazole-4-carbaldehyde was obtained in accordance with the method as described in Chem. Pharm. Bull. 1994, 42, 1784–1790.

b) 3-Methyl-5-phenylethynyl-3H-imidazole-4-carbaldehyde

The title compound, MS: m/e=210.6 (M+H$^+$) was prepared in accordance with the general method of example 1b from 5-bromo-3-methyl-3H-imidazole-4-carbaldehyde.

EXAMPLE 28

4-Phenylethynyl-1H-imidazole

The title compound, MS: m/e=169.2 (M+H$^+$) was prepared in accordance with the general method of example 1b from 4-bromoimidazole and ethynylbenzene.

EXAMPLE 29

1-Methyl-4-phenylethynyl-1H-imidazole

The title compound, MS: m/e=183.2 (M+H$^+$) was prepared in accordance with the general method of example 1b from 4-iodo-1-methyl-1H-imidazole.

EXAMPLE 30

1,2-Dimethyl-5-nitro-4-phenylethynyl-1H-imidazole a) 1,2-Dimethyl-4-iodo-5-nitroimidazole 1,2-Dimethyl-4-iodo-5-nitroimidazole was obtained according to the method as described in Aust. J. Chem. 1987, 40(8), 1399–413 b) 1,2-Dimethyl-5-nitro-4-phenylethynyl-1H-imidazole

The title compound, MS: m/e=242.4 (M+H$^+$) was prepared in accordance with the general method of example 1b from 1,2-dimethyl-4-iodo-5-nitroimidazole.

EXAMPLE 31

1,3-Dimethyl-5-phenylethynyl-1H-pyrazole a) 5-Iodo-1,3-dimethyl-1H-pyrazole

The title compound was obtained according to the method as described in Bull.Acad.Sci.USSR Div.Chem.Sci. (Engl.Transl.) 1983; 626–628 and in Izv.Akad.Nauk SSSR Ser.Khim. 1983; 688–690.

b) 1,3-Dimethyl-5-phenylethynyl-1H-pyrazole

The title compound, MS: m/e=196.8 (M+H$^+$) was prepared in accordance with the general method of example 1b from 5-iodo-1,3-dimethyl-1H-pyrazole.

EXAMPLE 32

4,5-Diisopropyl-1-methyl-2-styryl-1H-imidazole a) 4,5-Diisopropyl-1-methyl-1H-imidazole-2-carbaldehyde 4,5-Diisopropyl-1-methyl-1H-imidazole-2-carbaldehyde was obtained analogously to the method as described in Inorg. Chim. Acta 1999, 296(1), 208–221.

b) 4,5-Diisopropyl-1-methyl-2-styryl-1H-imidazole 194 mg (0.5 mmol) benzyltriphenylphosphoniumchloride and 97 mg (0.5 mmol) 4,5-diisopropyl-1-methyl-1H-imidazole-2-carbaldehyde were added to 1.3 ml of a 0.5 M solution of MeONa in MeOH. The mixture was shaken at 60° C. for 3 days, then cooled to room temperature. After addition of 0.2 ml formic acid, the title compound (59 mg, 44%, MS: m/e=269.4 [M+H$^+$]) was isolated from the reaction mixture by HPLC chromatography (YMC CombiPrep C18 column 5×20 mm, solvent gradient 10–95% CH$_3$CN in 0.1% TFA(aq) over 6.0 min, λ=230 nm, flow rate 40 ml/min).

EXAMPLE 33

2-[2-(4-Fluoro-phenyl)-vinyl]-4,5-diisopropyl-1-methyl-1H-imidazole

The title compound, MS: m/e=286.8 (M+H$^+$), was prepared in accordance with the general method of example 32b from 4-fluorobenzyl triphenylphosphonium chloride.

EXAMPLE 34

2-[2-(4-Chloro-phenyl)-vinyl]-4,5-diisopropyl-1-methyl-1H-imidazole

The title compound, MS: m/e=302.9 (M+H$^+$), was prepared in accordance with the general method of example 32b from 4-chlorobenzyl triphenylphosphonium chloride.

EXAMPLE 35

2-[2-(4-Butoxy-phenyl)-vinyl]-4,5-diisopropyl-1-methyl-1H-imidazole

The title compound, MS: m/e=340.9 (M+H$^+$), was prepared in accordance with the general method of example 32b from (4-butoxybenzyl)triphenylphosphonium bromide.

EXAMPLE 36

4,5-Diisopropyl-2-[2-(4-methoxy-2,3,6-trimethyl-phenyl)-vinyl]-1-methyl-1H-imidazole a) 2,3,6-Trimethyl-4-methoxybenzyltriphenyl-phosphonium chloride 2,3,6-Trimethyl-4-methoxybenzyltriphenyl-phosphonium chloride was obtained in accordance with the method as described in Liebigs Ann. Chem. 1984, 10, 1740–5.

b) 4,5-Diisopropyl-2-[2-(4-methoxy-2,3,6-trimethyl-phenyl)-vinyl]-1-methyl-1H-imidazole The title compound, MS: m/e=340.9 (M+H$^+$), was prepared in accordance with the general method of example 32b from 2,3,6-trimethyl-4-methoxybenzyltriphenyl-phosphonium chloride.

EXAMPLE 37

4,5-Diisopropyl-2-[2-(4-methoxy-phenyl)-vinyl]-1-methyl-1H-imidazole

The title compound, MS: m/e=298.9 (M+H$^+$), was prepared in accordance with the general method of example 32b from (4-methoxybenzyl)triphenylphosphonium bromide.

EXAMPLE 38

2-[2-(4-Chloro-3-fluoro-phenyl)-vinyl]-4,5-diisopropyl-1-methyl-1H-imidazole a) 4-Chloro-3-fluorobenzyl triphenylphosphonium bromide 4-Chloro-3-fluorobenzyl triphenylphosphonium bromide was obtained according to the method as described in EP 0 692 485.

b) 2-[2-(4-Chloro-3-fluoro-phenyl)-vinyl]-4,5-diisopropyl-1-methyl-1H-imidazole

The title compound, MS: m/e=320.8 (M+H$^+$), was prepared in accordance with the general method of example 32b from 4-chloro-3-fluorobenzyl triphenylphosphonium bromide.

EXAMPLE 39

2-[2-(4-Ethoxy-phenyl)-vinyl]-4,5-diisopropyl-1-methyl-1H-imidazole

The title compound, MS: m/e=312.9 (M+H$^+$), was prepared in accordance with the general method of example 32b from (4-ethoxybenzyl)triphenylphosphonium bromide.

EXAMPLE 40

4,5-Diisopropyl-1-methyl-2-[2-(2,3,4-trimethoxy-phenyl)-vinyl]-1H-imidazole a) Triphenyl-(2,3,4-trimethoxy-benzyl)-phosphonium bromide Triphenyl-(2,3,4-trimethoxy-benzyl)-phosphonium bromide was obtained according to the method as described in DE 43 07 049.

b) 4,5-Diisopropyl-1-methyl-2-[2-(2,3,4-trimethoxy-phenyl)-vinyl]-1H-imidazole

The title compound, MS: m/e=359.0 (M+H$^+$), was prepared in accordance with the general method of example 32b from triphenyl-(2,3,4-trimethoxy-benzyl)-phosphonium bromide.

EXAMPLE 41

2-[2-(2,4-Dichloro-phenyl)-vinyl]-4,5-diisopropyl-1-methyl-1H-imidazole

The title compound, MS: m/e=336.8 (M+H$^+$), was prepared in accordance with the general method of example 32b from 2,4dichlorobenzyltriphenylphosphonium chloride.

EXAMPLE 42

4,5-Diisopropyl-1-methyl-2-(2-p-tolyl-vinyl)-1H-imidazole

The title compound, MS: m/e=282.9 (M+H$^+$), was prepared in accordance with the general method of example 32b from 4-methylbenzyltriphenylphosphonium bromide.

EXAMPLE 43

4-Bromo-1-methyl-5-styryl-1H-imidazole a) 5-Bromo-3-methyl-3H-imidazole-4-carbaldehyde 5-Bromo-3-methyl-3H-imidazole-4-carbaldehyde was obtained by the method as described in Chem. Pharm. Bull. 1994, 42, 1784–1790.

b) 4-Bromo-1-methyl-5-styryl-1H-imidazole

The title compound, MS: m/e=263.0 (M+H$^+$), was prepared in accordance with the general method of example 21b from 5-bromo-3-methyl-3H-imidazole-4-carbaldehyde.

EXAMPLE 44

1-Methyl-5-styryl-1H-imidazole

The title compound was obtained according to the method as described in Chem. Pharm. Bull. 1987; 35, 823–828.

EXAMPLE A

Tablets of the following composition can be produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition can be produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition can be produced:

|  | mg/Capsule |
| --- | --- |
| Active ingredient | 50 |
| Crystalline, lactose | 60 |
| Microcrystalline cellulose | 34 |
| Talc | 5 |
| Magnesium stearate | 1 |
| Capsule fill weight | 150 |

The active ingredient would be prepared having a suitable particle size, then the crystalline lactose and the microcrystalline cellulose can be homogeneously mixed with one another, sieved and thereafter talc and magnesium stearate admixed. The final mixture can be filled into hard gelatine capsules of suitable size.

What is claimed is:

1. A method of treating Alzheimer's disease comprising administering to a person in need of such treatment a therapeutically effective amount of a compound of the formula

I

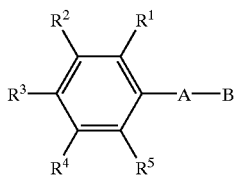

wherein
R¹, R², R³, R⁴ and R⁵ are independently selected from the group consisting of —(CH₂)ₙ-halogen, lower alkoxy, —(CH₂)ₙ—NRR', —(CH₂)ₙ—N(R)—C(O)-lower alkyl, aryl, unsubstituted heteroaryl or heteroaryl substituted by one or more lower alkyl;
R, R' and R" are independently selected from the group consisting of hydrogen or lower alkyl;
A is selected from the group consisting of —CH=CH— and —C≡C—; and
B is selected from the group consisting of

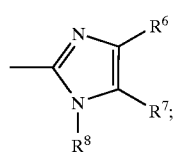
B1)

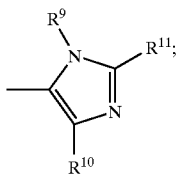
B2)

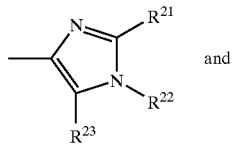
B5) and

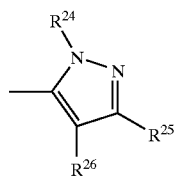
B6)

wherein
R⁶ is selected from the group consisting of lower alkyl, —(CH₂)ₙ—C(O)OR and halogen;
R⁷ is selected from the group consisting of lower alkyl, —(CH₂)ₙ—C(O)OR', halogen, nitro, unsubstituted heteroaryl and heteroaryl substituted by lower alkyl or cycloalkyl;
R⁸ is selected from the group consisting of lower alkyl, —(CH₂)ₙ—OH, —(CH₂)ₙ—C(O)OR" and aryl;
R⁹ is lower alkyl;
R¹⁰ is selected from the group consisting of lower alkyl and halogen;
R¹¹ is alkyl;
R²¹ is lower alkyl;
R²² is from the group consisting of lower alkyl and lower alkyl carrying at least one substituent selected from hydroxy and halogen;

R²³ is selected from the group consisting of lower alkyl, lower alkanoyl and nitro;
R²⁴, R²⁵ and R²⁶ are each independently lower alkyl; and
n is 0, 1, 2, 3, 4, 5 or 6;
or a pharmaceutically acceptable salt thereof.

2. A method of treating Alzheimer's disease comprising administering to a person in need of such treatment a therapeutically effective amount of a compound of the formula

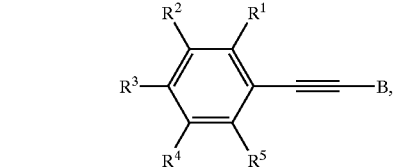
I-A wherein
R¹, R², R³, R⁴ and R⁵ are independently selected from the group consisting of —(CH₂)ₙ-halogen, lower alkoxy, —(CH₂)ₙ—NRR', —(CH₂)ₙ—N(R)—C(O)-lower alkyl, aryl, unsubstituted heteroaryl and heteroaryl substituted by one or more lower alkyl;
R, R' and R" are independently selected from the group consisting of, hydrogen or lower alkyl; and
B is selected from the group consisting of

B1)

B2)

B5) and

B6)

wherein
R⁶ is selected from the group consisting of lower alkyl, —(CH₂)ₙ—C(O)OR and halogen;
R⁷ is selected from the group consisting of lower alkyl, —(CH₂)ₙ—C(O)OR', halogen, nitro, unsubstituted heteroaryl and heteroaryl substituted by lower alkyl or cycloalkyl;
R⁸ is selected from the group consisting of lower alkyl, —(CH₂)ₙ—OH, —(CH₂)ₙ—C(O)OR" and aryl;

$R^9$ is lower alkyl;

$R^{10}$ is selected from the group consisting of lower alkyl and halogen;

$R^{11}$ is alkyl;

$R^{21}$ is lower alkyl:

$R^{22}$ is selected from the group consisting of lower alkyl and lower alkyl carrying at least one substituent selected from hydroxy and halogen;

$R^{23}$ is selected from the group consisting of lower alkyl, lower alkanoyl and nitro;

$R^{24}$, $R^{25}$ and $R^{26}$ are each independently lower alkyl; and n is 0, 1, 2, 3, 4, 5 or 6;

or a pharmaceutically acceptable salt thereof.

3. A method of treating pain comprising administering to a person in need of such treatment a therapeutically effective amount of a compound of formula

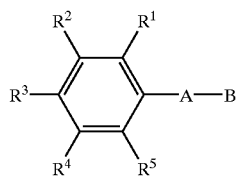

I wherein $R^1$, $R^2$, $R^3$, $R^4$ and $R^5$ are independently selected from the group consisting of hydrogen —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by one or more lower alkyl;

R, R' and R" are independently selected from the group consisting of hydrogen and lower alkyl;

A is selected from the group consisting of —CH=CH— and —C≡C—; and

B is selected from the group consisting of

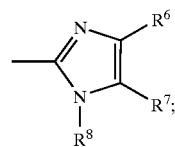

B1)

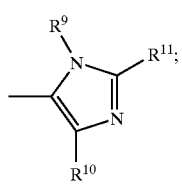

B2)

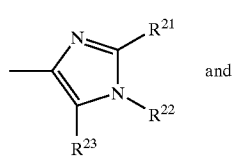

B5)

and

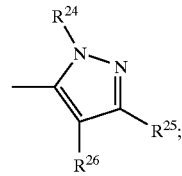

B6)

wherein $R^6$ is selected from the group consisting of lower alkyl, —$(CH_2)_n$—C(O)OR and halogen;

$R^7$ is selected from the group consisting of lower alkyl, —$(CH_2)_n$—C(O)OR', halogen, nitro, unsubstituted heteroaryl and heteroaryl substituted by lower alkyl or cycloalkyl;

$R^8$ is selected from the group consisting of lower alkyl, —$(CH_2)_n$—OH, —$(CH_2)_n$—C(O)OR" and aryl;

$R^9$ is lower alkyl;

$R^{10}$ is selected from the group consisting of lower alkyl and halogen;

$R^{11}$ is alkyl;

$R^{21}$ is lower alkyl;

$R^{22}$ is selected from the group consisting of lower alkyl and lower alkyl carrying at least one substituent selected from hydroxy and halogen;

$R^{23}$ is selected from the group consisting of lower alkyl, lower alkanoyl and nitro;

$R^{24}$, $R^{25}$ and $R^{26}$ are each independently lower alkyl; and n is 0, 1, 2, 3, 4, 5 or 6;

or a pharmaceutically acceptable salt thereof.

4. A method of treating anxiety or depression comprising administering to a person in need of such treatment a therapeutically effective amount of a compound of formula

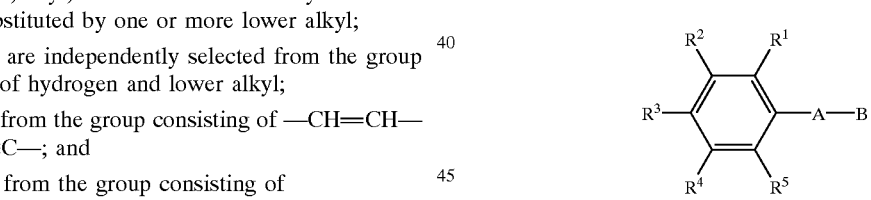

I wherein $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by one or more lower alkyl;

R, R' and R" are independently selected from the group consisting of hydrogen and lower alkyl;

A is selected from the group consisting of —CH=CH— and —C≡C—; and

B is selected from the group consisting of

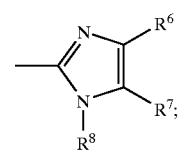

B1)

-continued

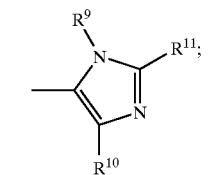
B2)

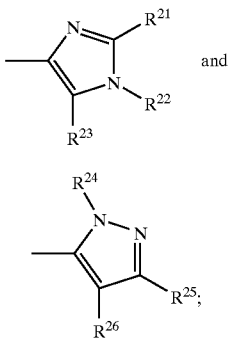
B5)

and

B6)

wherein
R⁶ is selected from the group consisting of lower alkyl, —(CH₂)ₙ—C(O)OR and halogen;
R⁷ is selected from the group consisting of lower alkyl, —(CH₂)ₙ—C(O)OR', halogen, nitro, unsubstituted heteroaryl and heteroaryl substituted by lower alkyl or cycloalkyl;
R⁸ is selected from the group consisting of lower alkyl, —(CH₂)ₙ—OH, —(CH₂)ₙ—C(O)OR" and aryl;
R⁹ is lower alkyl;
R¹⁰ is selected from the group consisting of lower alkyl and halogen;
R¹¹ is alkyl;
R²¹ is lower alkyl;
R²² is selected from the group consisting of lower alkyl carrying at least one substituent selected from hydroxy and halogen;
R²³ is selected from the group consisting of lower alkyl, lower alkanoyl and nitro;
R²⁴, R²⁵ and R²⁶ are each independently lower alkyl; and
n is 0, 1, 2, 3, 4, 5 or 6;
or a pharmaceutically acceptable salt thereof.

5. A method of treating pain comprising administering to a person in need of such treatment a therapeutically effective amount of a compound of the formula

I-A wherein
R¹, R², R³, R⁴ and R⁵ are independently selected from the group consisting of —(CH₂)ₙ-halogen, lower alkoxy, —(CH₂)ₙNRR', —(CH₂)ₙ—N(R)—C(O)-lower alkyl, aryl, unsubstituted heteroaryl and heteroaryl substituted by one or more lower alkyl;
R, R' and R" are independently selected from the group consisting of hydrogen or lower alkyl; and B is selected from the group consisting of

B1)

B2)

B5)

and

B6)

wherein

R⁶ is selected from the group consisting of lower alkyl, —(CH₂)ₙ—C(O)OR and halogen;

R⁷ is selected from the group consisting of lower alkyl, —(CH₂)ₙ—C(O)OR', halogen, nitro or unsubstituted heteroaryl and heteroaryl substituted by lower alkyl or cycloalkyl;

R⁸ is selected from the group consisting of lower alkyl, —(CH₂)ₙ—OH, —(CH₂)ₙ—C(O)OR" and aryl;

R⁹ is lower alkyl;

R¹⁰ is selected from the group consisting of lower alkyl and halogen;

R¹¹ is alkyl;

R²¹ is lower alkyl;

R²² is from the group consisting of lower alkyl and lower alkyl carrying least one substituent selected from hydroxy and halogen;

R²³ is selected from the group consisting of lower alkyl, alkanoyl and nitro;

R²⁴, R²⁵ and R²⁶ are each independently lower alkyl; and n is 0, 1, 2, 3, 4, 5 or 6;

or a pharmaceutically acceptable salt thereof.

6. A method of treating anxiety or depression comprising administering to a person in need of such treatment a therapeutically effective amount of a compound of the formula

I-A

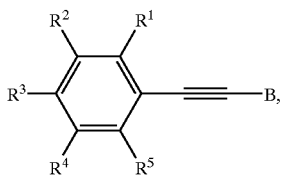

wherein
- $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by one or more lower alkyl;
- R, R' and R" are independently selected from the group consisting of hydrogen or lower alkyl; and
- B is selected from the group consisting of

B1)

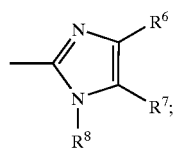

B2)

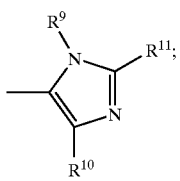

B5)

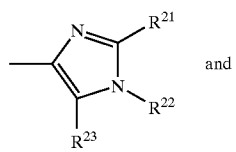 and

B6)

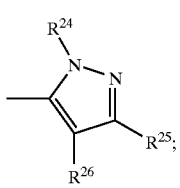

wherein
- $R^6$ is selected from the group consisting of lower alkyl, —$(CH_2)_n$—C(O)OR and halogen;
- $R^7$ is selected from the group consisting of lower alkyl, —$(CH_2)_n$—C(O)OR', halogen, nitro or unsubstituted heteroaryl and heteroaryl substituted by lower alkyl or cycloalkyl;
- $R^8$ is selected from the group consisting of lower alkyl, —$(CH_2)_n$—OH, —$(CH_2)_n$—C(O)OR" and aryl;
- $R^9$ is lower alkyl;
- $R^{10}$ is selected from the group consisting of lower alkyl and halogen;
- $R^{11}$ is alkyl;
- $R^{21}$ is lower alkyl;
- $R^{22}$ is selected from the group consisting of lower alkyl and lower alkyl carrying at least one substituent selected from hydroxy and halogen;

- $R^{23}$ is selected from the group consisting of lower alkyl, lower alkanoyl and nitro;
- $R^{24}$, $R^{25}$ and $R^{26}$ are each independently lower alkyl; and
- n is 0, 1, 2, 3, 4, 5 or 6;
or a pharmaceutically acceptable salt thereof.

7. A method of treating Alzheimer's disease comprising administering to the person in need of such treatment a therapeutically effective amount of a compound of the compound of formula

I-B

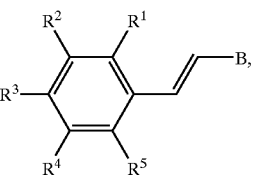

wherein
- $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by one or more lower alkyl residues;
- R, R' and R" are independently selected from the group consisting of hydrogen and lower alkyl; and
- B is selected from the group consisting of

B1)

B2)

B5) and

B6)

wherein
- $R^6$ is selected from the group consisting of lower alkyl, —$(CH_2)_n$—C(O)OR and halogen;
- $R^7$ is selected from the group consisting of lower alkyl, —$(CH_2)_n$—C(O)OR', halogen, nitro, and unsubstituted heteroaryl and heteroaryl substituted by lower alkyl or cycloalkyl;
- $R^8$ is selected from the group consisting of lower alkyl, —$(CH_2)_n$—OH, —$(CH_2)_n$—C(O)OR" and aryl;

$R^9$ is lower alkyl;

$R^{10}$ is selected from the group consisting of lower alkyl and halogen;

$R^{11}$ is alkyl;

$R^{21}$ is lower alkyl;

$R^{22}$ is selected from the group consisting of lower alkyl and lower alkyl carrying at least one substituent selected from hydroxy and halogen;

$R^{23}$ is selected from the group consisting of lower alkyl, lower alkanoyl and nitro;

$R^{24}$, $R^{25}$ and $R^{26}$ are each independently lower alkyl; and n is 0, 1, 2, 3, 4, 5 or 6;

or a pharmaceutically acceptable salt thereof.

8. A method of treating pain comprising administering to a person in need of such treatment a therapeutically effective amount of a compound of formula

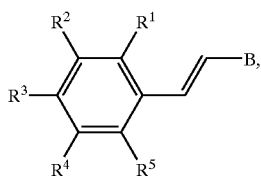

I-B wherein $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by one or more lower alkyl;

R, R' and R" are independently selected from the group consisting of hydrogen and lower alkyl; and B is selected from the group consisting of

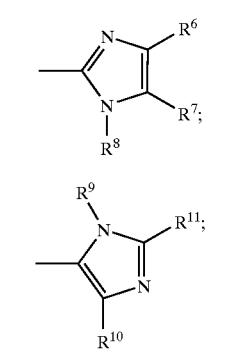

B1)

B2)

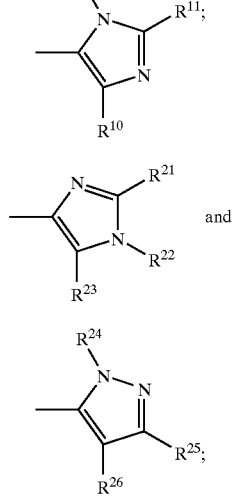

B5)

B6)

wherein $R^6$ is selected from the group consisting of lower alkyl, —$(CH_2)_n$—C(O)OR and halogen;

$R^7$ is selected from the group consisting of lower alkyl, —$(CH_2)_n$—C(O)OR', halogen, nitro, unsubstituted heteroaryl and heteroaryl substituted by lower alkyl or cycloalkyl;

$R^8$ is selected from the group consisting of lower alkyl, —$(CH_2)_n$—OH, —$(CH_2)_n$—C(O)OR" and aryl;

$R^9$ is lower alkyl;

$R^{10}$ is selected from the group consisting of lower alkyl and halogen;

$R^{11}$ is alkyl;

$R^{21}$ is lower alkyl;

$R^{22}$ is selected from the group consisting of lower alkyl and lower alkyl carrying at least one substituent selected from hydroxy and halogen;

$R^{23}$ is selected from the group consisting of lower alkyl, lower alkanoyl and nitro;

$R^{24}$, $R^{25}$ and $R^{26}$ are each independently lower alkyl; and n is 0, 1, 2, 3, 4, 5 or 6;

or a pharmaceutically acceptable salt thereof.

9. A method of treating anxiety or depression comprising administering to a person in need of such treatment a therapeutically effective amount of a compound of formula

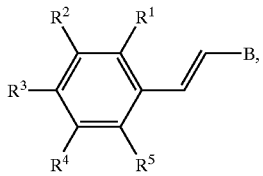

I-B wherein $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by one or more lower alkyl;

R, R' and R" are independently selected from the group consisting of hydrogen and lower alkyl; and B is selected from the group consisting of

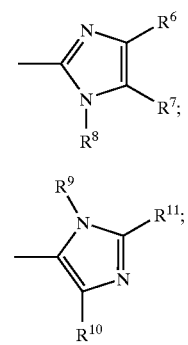

B1)

B2)

37

-continued

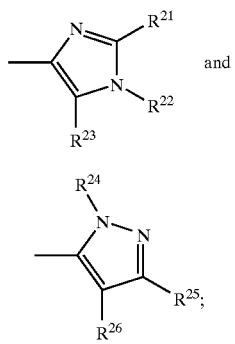

wherein
- $R^6$ is selected from the group consisting of lower alkyl, —$(CH_2)_n$—C(O)OR and halogen;
- $R^7$ is selected from the group consisting of lower alkyl, —$(CH_2)_n$—C(O)OR', halogen, nitro, unsubstituted heteroaryl and heteroaryl substituted by lower alkyl or cycloalkyl;
- $R^8$ is selected from the group consisting of lower alkyl, —$(CH_2)_n$—OH, —$(CH_2)_n$—C(O)OR" and aryl;
- $R^9$ is lower alkyl;
- $R^{10}$ is selected from the group consisting of lower alkyl and halogen;
- $R^{11}$ is alkyl;
- $R^{21}$ is lower alkyl;
- $R^{22}$ is from the group consisting of lower alkyl and lower alkyl carrying at least one substituent selected from hydroxy and halogen:
- $R^{23}$ is selected from the group consisting of lower alkyl, lower alkanoyl and nitro;
- $R^{24}$, $R^{25}$ and $R^{26}$ are each independently lower alkyl; and
- n is 0, 1, 2, 3, 4, 5 or 6;

or a pharmaceutically acceptable salt thereof.

10. A method of treating pain comprising administering to a person in need of such treatment a compound of formula

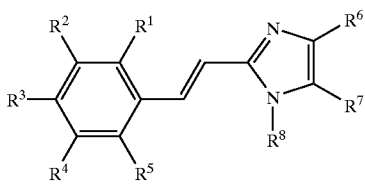

wherein
- $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by at least one lower alkyl;
- R, R' and R" are independently selected from the group consisting of hydrogen and lower alkyl;
- $R^6$ is selected from the group consisting of lower alkyl, —$(CH_2)_n$—C(O)OR and halogen;
- $R^7$ is selected from the group consisting of lower alkyl, —$(CH_2)_n$—C(O)OR', halogen, nitro, unsubstituted heteroaryl and heteroaryl substituted by lower alkyl or cycloalkyl; and
- $R^8$ is selected from the group consisting of lower alkyl, —$(CH_2)_n$—OH, —$(CH_2)_n$—C(O)OR" and aryl;

or a pharmaceutically acceptable salt thereof.

38

11. A method of treating anxiety or depression comprising administering to a person in need of such treatment a compound of formula

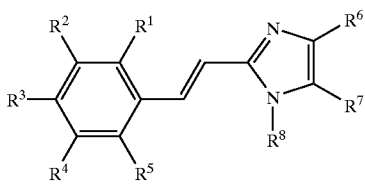

wherein
- $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by at least one lower alkyl;
- R, R' and R" are independently selected from the group consisting of hydrogen and lower alkyl;
- $R^6$ is selected from the group consisting of lower alkyl, —$(CH_2)_n$—C(O)OR and halogen;
- $R^7$ is selected from the group consisting of lower alkyl, —$(CH_2)_n$—C(O)OR', halogen, nitro, unsubstituted heteroaryl and heteroaryl substituted by lower alkyl or cycloalkyl; and
- $R^8$ is selected from the group consisting of lower alkyl, —$(CH_2)_n$—OH, —$(CH_2)_n$—C(O)OR" and aryl;

or a pharmaceutically acceptable salt thereof.

12. A method of treating pain comprising administering to a person in need of such treatment a therapeutically effective amount of a compound of formula

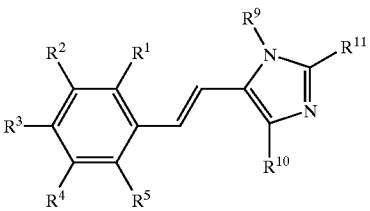

wherein
- $R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by at least one lower alkyl residues;
- R and R' are selected from the group consisting of hydrogen or lower alkyl;
- $R^9$ is lower alkyl;
- $R^{10}$ is halogen; and
- $R^{11}$ is or a pharmaceutically acceptable salt thereof.

13. A method of treating anxiety or depression comprising administering to a person in need of such treatment a therapeutically effective amount of a compound of formula

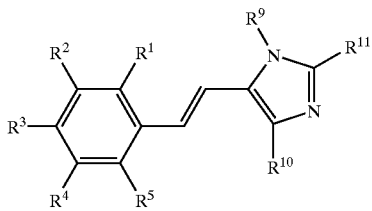

wherein
$R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by at least one lower alkyl residues;
R and R' are selected from the group consisting of hydrogen or lower alkyl;
$R^9$ is lower alkyl;
$R^{10}$ is halogen; and
$R^{11}$ is alkyl;
or a pharmaceutically acceptable salt thereof.

14. A method of treating Alzheimer's disease comprising administering to a person in need of such treatment a compound of formula

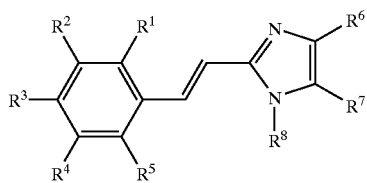

wherein
$R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by at least one lower alkyl;
R, R' and R" are independently selected from the group consisting of hydrogen and lower alkyl;
$R^6$ is selected from the group consisting of lower alkyl, —$(CH_2)_n$—C(O)OR and halogen;
$R^7$ is selected from the group consisting of lower alkyl, —$(CH_2)_n$—C(O)OR', halogen, nitro, unsubstituted heteroaryl and heteroaryl substituted by lower alkyl or cycloalkyl; and
$R^8$ is selected from the group consisting of lower alkyl, —$(CH_2)_n$—OH, —$(CH_2)_n$—C(O)OR" and aryl;
or a pharmaceutically acceptable salt thereof.

15. A method of treating Alzheimer's disease comprising administering to a person in need of such treatment a therapeutically effective amount of a compound of formula

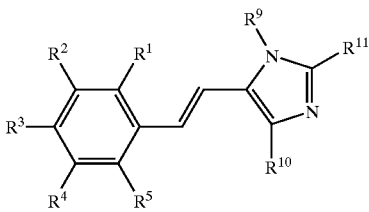

wherein
$R^1$, $R^2$, $R^3$, $R^4$ and $R^5$ are independently selected from the group consisting of —$(CH_2)_n$-halogen, lower alkoxy, —$(CH_2)_n$—NRR', —$(CH_2)_n$—N(R)—C(O)-lower alkyl, aryl, unsubstituted heteroaryl and heteroaryl substituted by at least one lower alkyl residues;
R and R' are selected from the group consisting of hydrogen or lower alkyl;
$R^9$ is lower alkyl;
$R^{10}$ is halogen; and
$R^{11}$ is or a pharmaceutically acceptable salt thereof.

* * * * *

UNITED STATES PATENT AND TRADEMARK OFFICE
CERTIFICATE OF CORRECTION

PATENT NO. : 6,927,232 B2
DATED : August 9, 2005
INVENTOR(S) : Vincent Mutel, Jens-Uwe Peters and Juergen Wichmann It is certified that error appears in the above-identified patent and that said Letters Patent is hereby corrected as shown below:

Title page,
Item [73], Assignee "Hoffman-La Roche Inc., Nutley, NJ (US)." should read
-- Hoffmann-La Roche Inc., Nutley, NJ (US) --.

Column 27,
Line 65, "$R^{22}$ is from the group" should read -- $R^{22}$ is selected from the group --.

Column 37,
Line 31, "$R^{22}$ is from the group" should read -- $R^{22}$ is selected from the group --.

Signed and Sealed this

Eleventh Day of October, 2005

JON W. DUDAS
*Director of the United States Patent and Trademark Office*